(12) United States Patent
Fujimoto et al.

(10) Patent No.: US 7,984,659 B2
(45) Date of Patent: Jul. 26, 2011

(54) DEVICE AND METHOD FOR MEASURING COMPRESSIVE FORCE OF FLEXIBLE LINEAR BODY

(75) Inventors: Hideo Fujimoto, Nagoya (JP); Akihito Sano, Nagoya (JP); Yoshitaka Nagano, Iwata (JP)

(73) Assignees: National Universtiy Corporation Nagoya, Aichi (JP); Institute of Technology NTN Corporation, Osaka (JP)

( * ) Notice: Subject to any disclaimer, the term of this patent is extended or adjusted under 35 U.S.C. 154(b) by 247 days.

(21) Appl. No.: 12/293,323

(22) PCT Filed: Mar. 19, 2007

(86) PCT No.: PCT/JP2007/055527
§ 371 (c)(1),
(2), (4) Date: Sep. 17, 2008

(87) PCT Pub. No.: WO2007/111182
PCT Pub. Date: Oct. 4, 2007

(65) Prior Publication Data
US 2009/0229381 A1    Sep. 17, 2009

(30) Foreign Application Priority Data

Mar. 27, 2006  (JP) ................. 2006-085317
Jul. 3, 2006  (JP) ................. 2006-183495

(51) Int. Cl.
*G01L 1/12* (2006.01)
*G01L 1/24* (2006.01)
(52) U.S. Cl. .................... 73/862.624; 73/800
(58) Field of Classification Search ......... 73/862.624–862.628, 862.324, 73/800
See application file for complete search history.

(56) References Cited

U.S. PATENT DOCUMENTS

| | | | |
|---|---|---|---|
| 4,570,354 A | | 2/1986 | Hindes |
| 4,856,529 A | * | 8/1989 | Segal ............................ 600/454 |
| 4,902,122 A | | 2/1990 | Azema et al. |
| 5,191,893 A | * | 3/1993 | Reiten .......................... 600/534 |

(Continued)

FOREIGN PATENT DOCUMENTS

DE        43 24 513 A1    1/1995

(Continued)

OTHER PUBLICATIONS

European Search Report issued in European Patent Application No. 07738972.4-1265/2000789 PCT/JP2007/055527, dated Jan. 28, 2010.

(Continued)

*Primary Examiner* — Max Noori
(74) *Attorney, Agent, or Firm* — McDermott Will & Emery LLP

(57) ABSTRACT

A measurement device can detect a degree of bending of a linear body with a sensor when compressive force in a direction of longitudinal axis is applied to the linear body as a result of contact of a tip end of the linear body with an obstacle. Then, the detected degree of bending of the linear body is converted to compressive force in the direction of longitudinal axis applied to the linear body based on predetermined correlation between the degree of bending and the compressive force, so that presence of an obstacle in a direction of travel of the linear body can be sensed based on increase in the compressive force. In addition, as the same measurement device is applicable to linear bodies of various shapes and materials, cost effectiveness is achieved.

17 Claims, 17 Drawing Sheets

U.S. PATENT DOCUMENTS

| | | | |
|---|---|---|---|
| 5,374,821 A * | 12/1994 | Muhs et al. | 250/227.16 |
| 5,538,364 A * | 7/1996 | Huntsman | 405/288 |
| 5,685,329 A * | 11/1997 | Taylor | 137/71 |
| 5,931,805 A * | 8/1999 | Brisken | 604/22 |
| 6,096,004 A | 8/2000 | Meglan et al. | |
| 6,272,371 B1 * | 8/2001 | Shlomo | 600/424 |
| 6,530,889 B1 * | 3/2003 | Konings et al. | 600/486 |
| 6,612,992 B1 * | 9/2003 | Hossack et al. | 600/467 |
| 6,970,730 B2 * | 11/2005 | Fuimaono et al. | 600/374 |
| 6,981,945 B1 | 1/2006 | Sarvazyan et al. | |
| 7,072,720 B2 * | 7/2006 | Puskas | 607/118 |
| 7,277,162 B2 * | 10/2007 | Williams | 356/32 |
| 7,373,721 B2 * | 5/2008 | Bergamasco et al. | 33/1 N |
| 2008/0275369 A1 * | 11/2008 | Fandriks | 600/593 |

FOREIGN PATENT DOCUMENTS

| | | |
|---|---|---|
| JP | 59-47241 | 11/1984 |
| JP | 10-263089 | 10/1998 |
| JP | 11-072312 | 3/1999 |
| JP | 2000-42116 | 2/2000 |
| JP | 2001-215158 | 8/2001 |
| JP | 2002-29381 | 1/2002 |
| JP | 2005-010064 | 1/2005 |
| JP | 2006-017664 | 1/2006 |
| JP | 2006-64465 | 3/2006 |
| WO | WO 2006/020792 A2 | 2/2006 |

OTHER PUBLICATIONS

M.N. Appleyard et al., "The measurement of forces exerted during colonoscopy," Gastrointestinal Endoscopy, Elsevier, NL, vol. 52, No. 2, 2008, pp. 237-240.

S. Dogramadzi et al., "Recording forces exerted on the bowel wall during colonoscopy: in vitro evaluation," Int Medical Robotics and Computer Assisted Surgery 2005, vol. 1, No. 4, 2005, pp. 89-97.

M. Lazeroms et al., "Optical Fibre Force Sensor for Minimal-Invasive-Surgery Grasping Instruments," Engineering in Medicine and Biology Society, 1996, IEEE, vol. 1, pp. 234-235.

M. Tanimoto et al., "Micro Force Sensor for Intravascular Neurosurgery," Robotics and Automation, 1997, IEEE vol. 2, pp. 1561-1562.

Mosse, C.A., et al., "Device for measuring the forces exerted on the shaft of an endoscope during colonoscopy", Medical & Biological Engineering & Computing, Mar. 1998, pp. 186-190, vol. 36.

* cited by examiner

DEVICE AND METHOD FOR MEASURING COMPRESSIVE FORCE OF FLEXIBLE LINEAR BODY

RELATED APPLICATIONS

This application is the U.S. National Phase under 35 U.S.C. §371 of International Application No. PCT/JP2007/055527, filed on Mar. 19, 2007, which in turn claims the benefit of Japanese Application No. 2006-085317, filed on Mar. 27, 2006 and Japanese Application No. 2006-183495, filed on Jul. 3, 2006, the disclosures of which Applications are incorporated by reference herein.

TECHNICAL FIELD

The present invention relates to a measurement device and a measurement method and particularly to a device and a method for measuring compressive force applied to a linear body having flexibility.

BACKGROUND ART

A linear body having flexibility has been put into practical use as a linear medical appliance inserted in a vessel in a body. For example, a guide wire or a catheter inserted in a vessel in a body such as a blood vessel, a ureter, a bronchus, an alimentary canal, or a lymph vessel, or a wire having an embolus coil attached at a tip end for embolizing an aneurysm has been known. Such a linear body is inserted into a vessel in a body and guided to a destination through an operation from outside the body.

In many cases, the vessel in which the linear body is inserted is not necessarily linear but partially flexed or branched. In addition, a diameter of the vessel is not necessarily uniform, and the vessel itself may become thinner or a diameter of the vessel may be made smaller by an obstacle located in the vessel such as a thrombus in a blood vessel. A conventional linear body, however, has not been provided with means for sensing a condition in a direction of travel of the linear body, and it has been necessary to use operator's intuition in operating the linear body and the operator has had to be skilled in the operation for guiding the linear body from outside the body. A device provided with a pressure sensor at a tip end of a linear body is disclosed as a device sensing presence of an obstacle in a direction of travel of the linear body (see, for example, Japanese Patent Laying-Open No. 10-263089 (Patent Document 1)).

Patent Document 1: Japanese Patent Laying-Open No. 10-263089

DISCLOSURE OF THE INVENTION

Problems to be Solved by the Invention

On the other hand, it is difficult to realize a device provided with a pressure sensor at the tip end of a linear body, in particular when the linear body is extremely thin. For example, a guide wire to be inserted in a cerebral blood vessel has a diameter around 0.35 mm, and it is difficult to provide a small pressure sensor at the tip end of such an extremely thin linear body. In addition, it is more difficult to insert a wire in the linear body in order to extract a signal from the pressure sensor to the outside.

Moreover, if the vessel in which the linear body is inserted is flexed or if a diameter of the vessel is small, insertion resistance of the linear body is affected by friction with the vessel. Accordingly, an output from the pressure sensor provided at the tip end of the linear body may not necessarily be in agreement with kinesthetic sense of the operator at the time of insertion. Therefore, even when the device provided with the pressure sensor at the tip end of the linear body is used, the operator operates the linear body based on kinesthetic sense information of the insertion resistance of the linear body externally held with fingers of the operator, that is, relying on intuition of the operator. Further, as it is only the operator that can feel the kinesthetic sense, it is difficult to quantify manipulation of a skilled operator so as to transfer the skill to a less experienced operator.

In addition, it is not cost effective to prepare linear bodies of various shapes and materials for adaptation to different applications and to provide pressure sensors in respective linear bodies, and manufacturing cost is increased.

Therefore, a main object of the present invention is to provide a measurement device and a measurement method capable of sensing presence of an obstacle in a direction of travel of a linear body, that are applicable to linear bodies of various shapes and materials.

Means for Solving the Problems

A measurement device according to the present invention is a measurement device measuring compressive force in a direction of longitudinal axis applied to a linear body having flexibility, and includes a main body in which a through hole through which the linear body passes is formed, the linear body being bent in a prescribed direction within the through hole when the compressive force in the direction of longitudinal axis is applied to the linear body. In addition, the measurement device includes a sensor detecting a degree of bending of the linear body. Moreover, the measurement device includes a conversion circuit converting the degree of bending detected by the sensor into the compressive force in the direction of longitudinal axis applied to the linear body.

Here, the sensor can detect a degree of bending of the linear body when compressive force in the direction of longitudinal axis is applied to the linear body as a result of contact of the tip end of the linear body with the obstacle. Then, the detected degree of bending of the linear body is converted into compressive force in the direction of longitudinal axis applied to the linear body based on predetermined correlation between the degree of bending of the linear body and the compressive force applied to the linear body, so that presence of the obstacle in a direction of travel of the linear body can be sensed based on increase in the compressive force. Here, the sensor is provided in a position where the linear body is operated, located outside the vessel in which the linear body is inserted, so as to measure the compressive force in the direction of longitudinal axis applied to the linear body. Therefore, the compressive force applied to the linear body can quantitatively be measured also in regard to an extremely thin linear body where it is difficult to provide a pressure sensor at the tip end. In addition, as the same measurement device is applicable to linear bodies of various shapes or materials, the linear body as used so far can be used without modification, which leads to cost effectiveness.

Preferably, the linear body above is a linear medical appliance to be inserted in a vessel in a body. Here, contact of the tip end of the linear body with an inner wall of the vessel can be sensed by measuring increase in the compressive force in the direction of longitudinal axis applied to the linear body. Therefore, application of excessive load onto the vessel within the body can be prevented.

In addition, preferably, the sensor above is an optical sensor including a light source emitting light and a light receiver receiving light emitted by the light source. Then, the sensor detects the degree of bending of the linear body using a quantity of light received by the light receiver with respect to a quantity of light emitted by the light source. Here, the degree of bending of the linear body can more reliably be detected, and by converting the degree of bending, the compressive force applied to the linear body can more reliably be measured.

In addition, preferably, the sensor above is an optical array sensor including a light source emitting light and a light receiver receiving light emitted by the light source. Then, the sensor detects the degree of bending of the linear body by detecting a position at which light emitted by the light source is cut off by the linear body and a quantity of light received by the light receiver decreases. Here, the degree of bending of the linear body can more reliably be detected, and by converting the degree of bending, the compressive force applied to the linear body can more reliably be measured.

In addition, preferably, the sensor includes a detection electrode and a capacitance detection circuit detecting the degree of bending of the linear body based on a capacitance generated between the detection electrode and the linear body.

In addition, preferably, the sensor includes a light source, an objective lens directing light from the light source to the linear body, a moving portion moving the objective lens, an objective lens position detection unit detecting a position of the objective lens, a light receiver receiving light reflected by the linear body and converting the light into an electric signal, and an operation unit detecting the degree of bending of the linear body based on the detected position of the objective lens and the electric signal from the light receiver.

In addition, preferably, the sensor includes a light source emitting light to the linear body, and an image processing unit receiving light reflected by the linear body, picking up an image of the linear body, and detecting the degree of bending of the linear body based on the picked-up image of the linear body.

In addition, preferably, the sensor includes a piezoelectric element outputting ultrasound to the linear body and receiving the ultrasound reflected by the linear body, and a time difference detection unit detecting a time period from output of the ultrasound by the piezoelectric element to the linear body until reception of the ultrasound reflected by the linear body and detecting the degree of bending of the linear body based on the detected time period.

In addition, preferably, the linear body is a conductor or a magnetic element, and the sensor further includes a coil, a voltage supply circuit supplying a voltage to the coil, and a waveform detection circuit detecting an amplitude of a waveform of a current that flows through the coil or a phase difference between a waveform of the voltage supplied to the coil and the waveform of the current that flows through the coil, and detecting the degree of bending of the linear body based on a result of detection.

In addition, preferably, the linear body is a magnetic element, and the sensor further includes a magnet and a magnetic detection unit detecting magnetic flux from the magnet and detecting the degree of bending of the linear body based on a result of detection.

In addition, preferably, the sensor further includes a movable portion coupled to the linear body, and a movable portion position detection unit detecting a position of the movable portion and detecting the degree of bending of the linear body based on a result of detection.

In addition, preferably, the measurement device includes a plurality of sensors, and the conversion circuit converts the degree of bending detected by the plurality of sensors into the compressive force applied to the linear body.

In addition, preferably, the measurement device above includes at least any one of a visualizing instrument displaying an output from the sensor and an auralizing instrument converting variation in the output from the sensor into voice and sound. Here, kinesthetic sense of the operator can be quantified for display and record. Therefore, manipulation of a skilled operator can quantitatively be transferred to a less experienced operator. Moreover, the operator can reliably recognize the time when compressive force applied to the linear body is equal to or greater than a predetermined threshold value.

In addition, preferably, the measurement device above is incorporated in medical equipment for use. For example, when the measurement device is incorporated in a Y-connector for use, the linear body is operated through an input port of the Y-connector and a medicine can be injected through another input port.

In addition, preferably, the measurement device above is attached to a training simulator simulating a human body for use. Here, manipulation of a skilled operator can be quantified and manipulation can quantitatively be transferred to a less experienced operator. Therefore, manipulation of the less experienced operator can quickly be improved.

A measurement method according to the present invention is a method of measuring compressive force in a direction of longitudinal axis applied to a linear body having flexibility, and the method includes the step of detecting, by using a sensor, a degree of bending of the linear body in a prescribed direction when the compressive force is applied to the linear body. In addition, the method includes the step of converting the degree of bending of the linear body detected in the detecting step into the compressive force applied to the linear body based on predetermined correlation between the degree of bending of the linear body and the compressive force applied to the linear body.

Here, the sensor can detect a degree of bending of the linear body when compressive force in the direction of longitudinal axis is applied to the linear body as a result of contact of the tip end of the linear body with the obstacle. Then, the detected degree of bending of the linear body is converted into compressive force in the direction of longitudinal axis applied to the linear body based on predetermined correlation between the degree of bending of the linear body and the compressive force applied to the linear body, so that presence of the obstacle in a direction of travel of the linear body can be sensed based on increase in the compressive force.

Effects of the Invention

As described above, according to the measurement device of the present invention, the sensor can detect a degree of bending of the linear body when compressive force in the direction of longitudinal axis is applied to the linear body as a result of contact of the tip end of the linear body with the obstacle. Then, the detected degree of bending of the linear body is converted into compressive force in the direction of longitudinal axis applied to the linear body, so that presence of the obstacle in a direction of travel of the linear body can be sensed based on increase in the compressive force. In addition, as the same measurement device is applicable to linear bodies of various shapes or materials, cost effectiveness is achieved.

DESCRIPTION OF THE REFERENCE SIGNS

Figure 1:
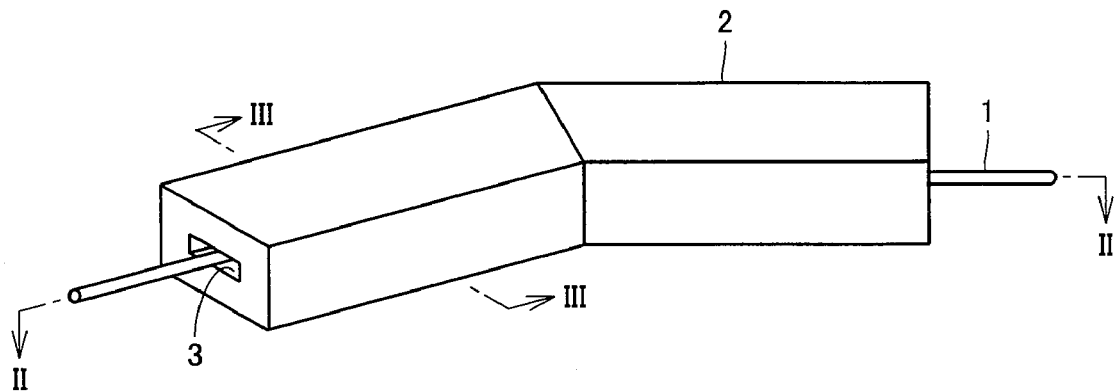
FIG. 1 is a schematic diagram showing appearance of a main body of a measurement device according to Embodiment 1 of the present invention.

1 linear body; 2 measurement device main body; 3 through hole; 4 input/output port; 5 restraint portion; 6 space; 7 sensor; 8 light source; 9 light receiver; 10 illumination control circuit; 11 amplifier circuit; 12, 161, 162 conversion circuit; 13 selector; 14 Y-connector; 15 input port; 16 another input port; 17 output port; 18 visualizing instrument; 19 visualizing instrument; 20 auralizing instrument; 21 speaker; 22 guide wire; 23 catheter; 24 operator; 25 human body; 26 simulator; 27 simulated perspective image; 28 cable; 29 light source; 30 light receiver; 31 compressive force output device; 41 displacement sensor; 42 capacitance sensor; 43 detection electrode; 44 guard electrode; 45 capacitance detection circuit; 32, 51, 61 optical sensor; 52, 62 semiconductor laser (light source); 53 half mirror; 54 collimating lens; 55 objective lens; 56 tuning fork (moving portion); 57 tuning fork position detection unit (objective lens position detection unit); 58 pinhole; 59 light-receiving element (light receiver); 60 operation unit; 63 light-transmissive lens; 64 light-receiving lens; 65 image processing unit; 71 ultrasonic sensor; 72 time difference detection unit; 73 piezoelectric element; 81 eddy current sensor; 82 detection coil; 83 voltage supply circuit; 84 waveform detection circuit; 91 magnetic sensor; 92 detection coil; 93 voltage supply circuit; 94 waveform detection circuit; 101 magnetic sensor; 102 Hall sensor (magnetic detection unit); 103 amplifier circuit; 104 permanent magnet; 111 contact sensor; 112 pulley; 113 stopper; 114 spring; 115 movable portion position detection unit; 116 encoder; 117 optical sensor; 118 resistor; 119 conductor; 120 resistance value detection unit; 121 contact sensor; 122 ring; 123 connection portion; 124 movable portion position detection unit; 131, 141, 151 to 153 displacement sensor; 132 measurement unit; 133 detection circuit; 142 measurement unit; 143 detection circuit; and 201 to 217 measurement device.

BEST MODES FOR CARRYING OUT THE INVENTION

An embodiment of the present invention will be described hereinafter with reference to the drawings. In the drawings below, the same or corresponding elements have the same reference characters allotted and detailed description thereof will not be repeated.

Embodiment 1

FIG. 1 is a schematic diagram showing appearance of a main body of a measurement device according to Embodiment 1 representing one embodiment of the present invention. In FIG. 1, a measurement device 201 includes a measurement device main body 2, and in measurement device main body 2, a through hole 3 through which linear body 1 having flexibility passes is formed.

Figure 2:
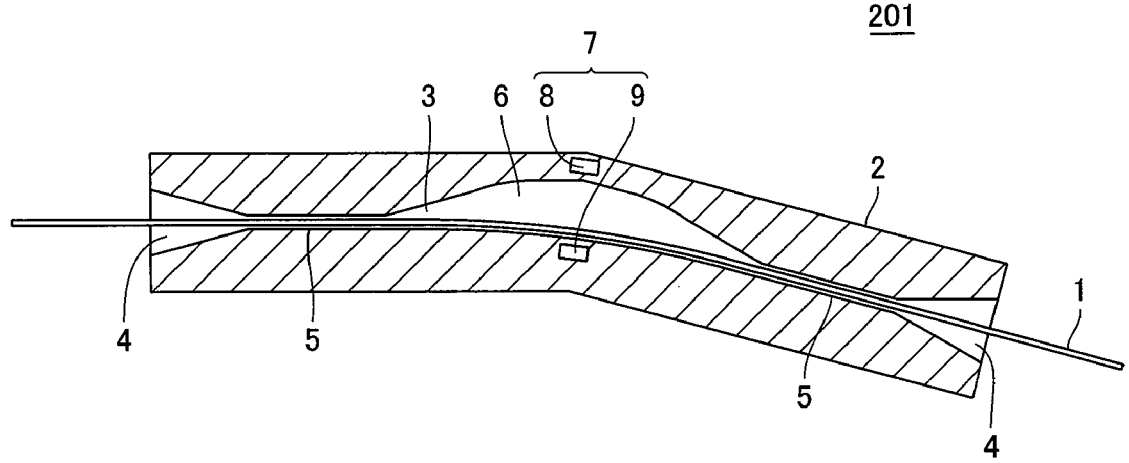
FIG. 2 is a cross-sectional schematic diagram showing an internal structure of the main body of the measurement device shown in FIG. 1.
Figure 3:
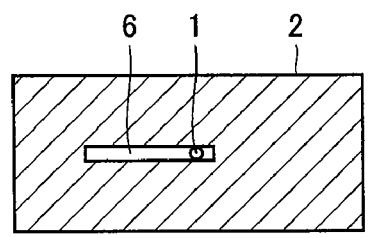
FIG. 3 is a cross-sectional view showing a cross-section along the line III-III in FIG. 1.

FIG. 2 is a cross-sectional schematic diagram showing an internal structure of the main body of the measurement device shown in FIG. 1. FIG. 3 is a cross-sectional view showing a cross-section along the line III-III in FIG. 1. In FIG. 2, at an inlet and an outlet of through hole 3, a tapered input/output port 4 is formed in order to facilitate insertion, by making greater the inlet and the outlet where linear body 1 passes. In a restraint portion 5 within measurement device main body 2, a diameter of through hole 3 is slightly greater than a diameter of linear body 1 (for example, 105% to 120% of the diameter of linear body 1), and a length of through hole 3 along a direction of longitudinal axis of linear body 1 is at least several times as great as the diameter of linear body 1. Therefore, movement of linear body 1 in restraint portion 5 in a direction other than the direction of longitudinal axis is restricted.

Measurement device main body 2 defines a direction of bending of linear body 1 within through hole 3 when compressive force in the direction of longitudinal axis is applied to linear body 1. Namely, through hole 3 curves between two restraint portions 5, and linear body 1 passes through through hole 3 while bending along one wall. In addition, through hole 3 on a wall side, along which linear body 1 does not extend, opens up to form a space 6.

In space 6, movement of linear body 1 in a direction in parallel to the drawing page surface is not restricted. In input/output port 4 and space 6, a height of through hole 3 in a direction perpendicular to the drawing page surface is slightly greater than the diameter of linear body 1 (for example, 105% to 120% of the diameter of linear body 1), and movement of linear body 1 in the direction perpendicular to the drawing page surface is restricted. Namely, in input/output port 4 and space 6, a cross-sectional shape of through hole 3 in a direction perpendicular to the direction of longitudinal axis of linear body 1 is rectangular. The direction of bending of linear body 1 within through hole 3 is thus defined, to thereby position a bending portion of linear body 1 when compressive force in the direction of longitudinal axis is applied to linear body 1.

Figure 4:
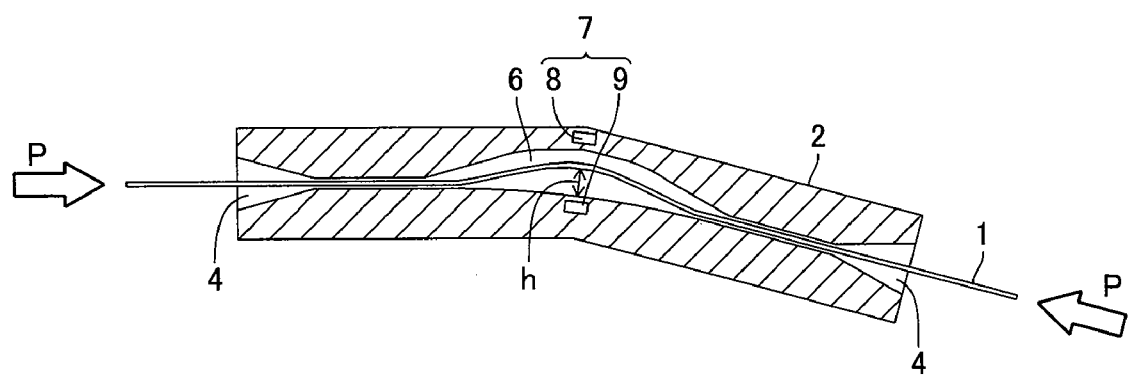
FIG. 4 is a cross-sectional schematic diagram showing bending of a linear body within the measurement device when compressive force is applied to the linear body.

FIG. 4 is a cross-sectional schematic diagram showing bending of linear body 1 within measurement device main body 2 when compressive force is applied to linear body 1. In FIG. 4, when compressive force P in the direction of longitudinal axis is applied to linear body 1, linear body 1 bends in a prescribed direction in space 6 within through hole 3, that is, toward the wall side along which linear body 1 does not extend in space 6. When linear body 1 is bent, a height h of peak of bending, that is, a distance from the wall surface along which linear body 1 extends to linear body 1 increases. Measurement device main body 2 includes an optical sensor 7 in the direction of height of the peak of bending, for detecting a degree of bending of linear body 1. Sensor 7 includes a light source 8 (such as an infrared LED) emitting light and a light receiver 9 (such as a phototransistor) arranged at a position opposed to light source 8 in space 6 and receiving light emitted by light source 8. As shown in FIG. 4, light source 8 and light receiver 9 are arranged to be opposed to each other in a longitudinal direction in the rectangular cross-section of through hole 3, with linear body 1 lying therebetween. When h is small, as linear body 1 is located in the vicinity of light receiver 9, linear body 1 forms a large image that cuts off light over light receiver 9 and a quantity of light received by light receiver 9 decreases. When compressive force P is applied to linear body 1 to bend linear body 1 and h becomes greater, linear body 1 moves away from light receiver 9 and therefore the quantity of light received by light receiver 9 increases. Therefore, height h of the peak of bending of linear body 1, that is, the degree of bending of linear body 1, can be detected by using the quantity of light received by light receiver 9 with respect to the quantity of light emitted by light source 8.

Figure 5:
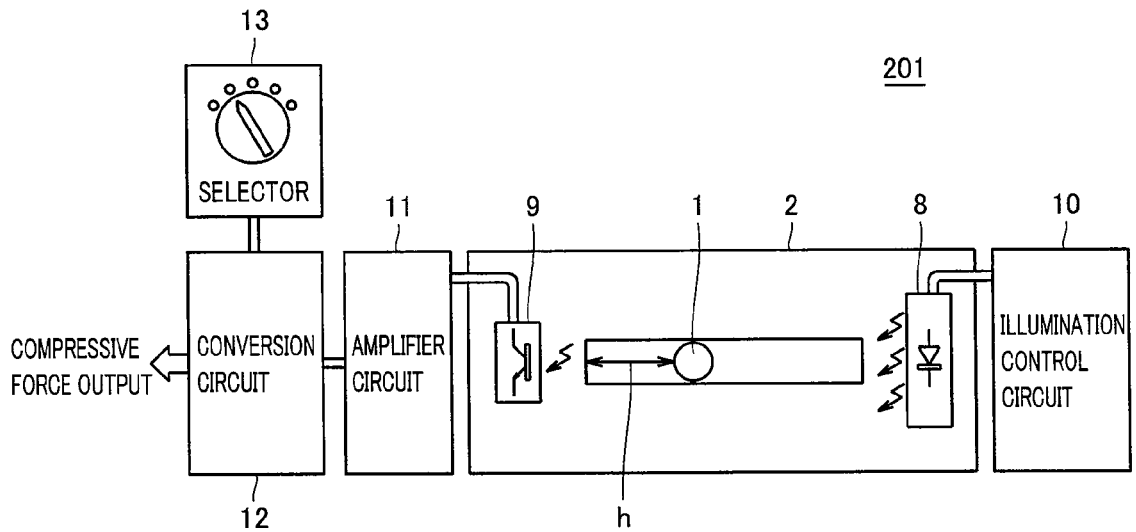
FIG. 5 is a schematic diagram showing an overall configuration of the measurement device.

A specific operation of the measurement device will now be shown. FIG. 5 is a schematic diagram showing an overall configuration of the measurement device. In FIG. 5, measurement device 201 includes an illumination control circuit 10 causing light source 8 to emit light and an amplifier circuit 11 amplifying an output from light receiver 9, in addition to measurement device main body 2. Moreover, measurement device 201 also includes a conversion circuit 12 converting the degree of bending of linear body 1 detected based on the quantity of light received by light receiver 9 with respect to the quantity of light emitted by light source 8 into compressive force in the direction of longitudinal axis applied to linear body 1. In measurement device main body 2, an optical path from light source 8 to light receiver 9 is formed of a material through which light used for detection is transmitted.

Figure 6:
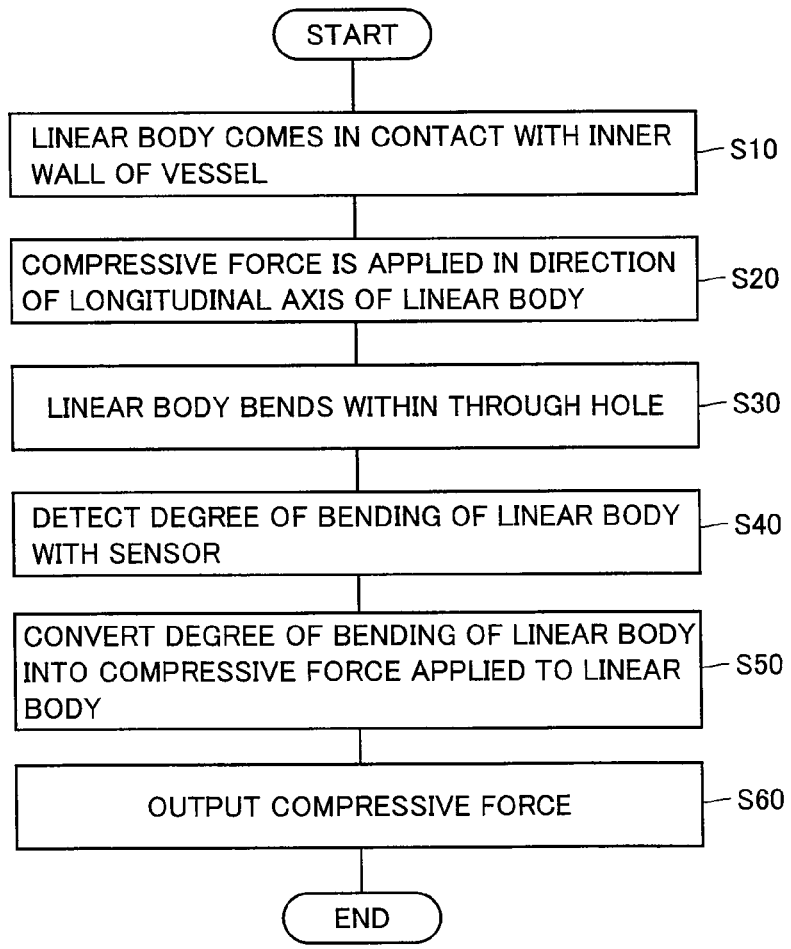
FIG. 6 is a flowchart showing a method of measuring compressive force applied to the linear body.

FIG. 6 is a flowchart showing a method of measuring compressive force applied to linear body 1. A method of measuring compressive force applied to linear body 1 as a result of contact of the tip end of linear body 1 with the inner wall of the vessel when linear body 1 is inserted in the vessel and operated from the outside of the vessel will be described with reference to FIG. 6. Initially, in the step (S10), the tip end of linear body 1 inserted in the vessel and operated from the outside of the vessel comes in contact with the inner wall of the vessel. Then, in the step (S20), when force is applied in the direction of longitudinal axis from the outside of the vessel in order to insert linear body 1 further, the operation of linear body 1 is restricted because the tip end of linear body 1 comes in contact with the inner wall of the vessel. Accordingly, compressive force is applied in the direction of longitudinal axis of linear body 1. Then, in the step (S30), linear body 1 bends, as a result of application of compressive force, toward the wall side along which linear body 1 does not extend in space 6 within through hole 3. Then, in the step (S40), the degree of bending of linear body 1 is detected with sensor 7, based on the quantity of light received by light receiver 9 with respect to the quantity of light emitted by light source 8. Then, in step (S50), the degree of bending of linear body 1 is converted into compressive force applied to linear body 1, based on predetermined correlation between the degree of bending of linear body 1 and compressive force applied to linear body 1. Then, in the step (S60), compressive force obtained by converting the degree of bending of linear body 1 is output.

Figure 7:
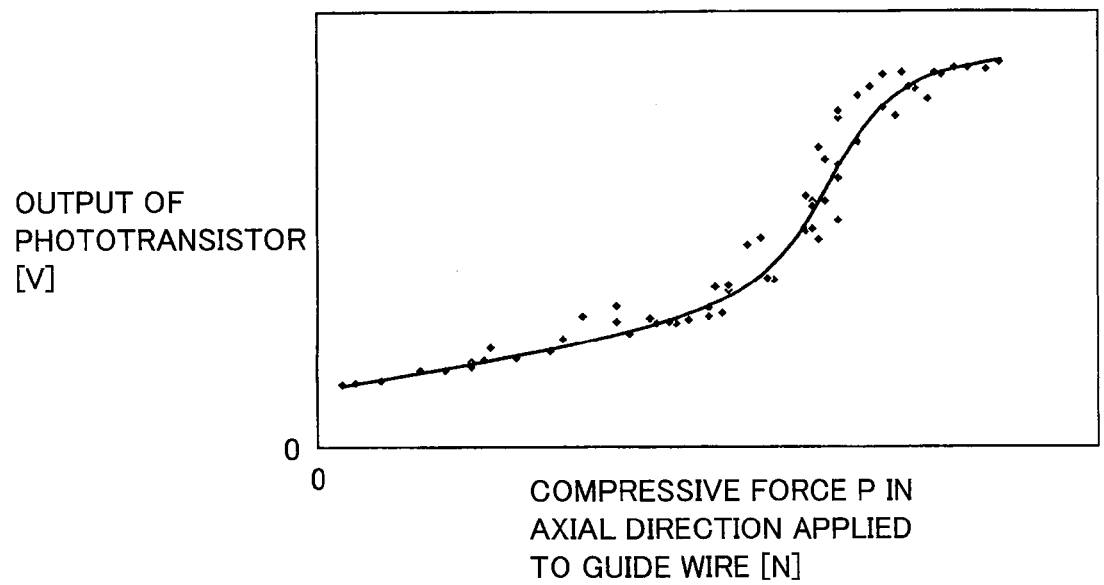
FIG. 7 is a graph showing an example of measurement of an output from a phototransistor with respect to compressive force applied to a guide wire.

FIG. 7 shows an example of determination of correlation between the degree of bending of linear body 1 and compressive force applied to linear body 1 used in the step (S50). Namely, it is a graph showing an example of measurement of an output from a phototransistor with respect to compressive force in the direction of longitudinal axis applied to a guide wire when the guide wire is employed as linear body 1 and the phototransistor is employed as light receiver 9. In FIG. 7, the abscissa represents compressive force in the direction of longitudinal axis applied to the guide wire. In addition, the ordinate represents a voltage output obtained by converting, with the use of the phototransistor, the quantity of light received by the phototransistor in correspondence with compressive force applied to the guide wire. When compressive force is not applied to linear body 1, linear body 1 bends along one wall of through hole 3. Here, as linear body 1 casts shadow over a light-receiving surface of light receiver 9, the quantity of light emitted by light source 8 that can be received by light receiver 9 is not large. Accordingly, the output of the phototransistor is small, which shows that height h of the peak of bending of linear body 1 is close to 0, that is, the compressive force is not applied to linear body 1.

When the degree of bending becomes greater as a result of application of compressive force to linear body 1, height h of the peak of bending becomes greater. Here, the image of linear body 1 that cuts off light over the light-receiving surface of light receiver 9 becomes smaller. Namely, the quantity of light that goes around linear body 1 and reaches the light-receiving surface of light receiver 9 increases. Then, the quantity of light received from light source 8 by light receiver 9 increases. Therefore, the output of the phototransistor increases, which shows that height h of the peak of bending of linear body 1 is great, that is, the compressive force is applied to linear body 1.

The correlation between compressive force applied to the guide wire and the output of the phototransistor shown in FIG. 7 is determined in advance and stored in conversion circuit 12. Then, the output from the phototransistor is amplified by amplifier circuit 11, which is in turn converted to compressive force by using the aforementioned correlation stored in conversion circuit 12. Compressive force in the direction of longitudinal axis applied to linear body 1 can thus be measured.

Thus, the degree of bending of linear body 1 when compressive force in the direction of longitudinal axis is applied to linear body 1 as a result of contact of the tip end of linear body 1 with an obstacle such as the inner wall of the vessel in which linear body 1 is inserted can be detected with sensor 7. Then, conversion circuit 12 converts the detected degree of bending of linear body 1 into compressive force in the direction of longitudinal axis applied to linear body 1. Accordingly, as the compressive force applied to linear body 1 increases, presence of the obstacle in the direction of travel of linear body 1 can be sensed. Here, sensor 7 is provided in a position where linear body 1 is operated, located outside the vessel in which linear body 1 is inserted, so as to measure compressive force in the direction of longitudinal axis applied to linear body 1. Therefore, compressive force can quantitatively be measured also in regard to very thin linear body 1 in which it is difficult to provide a pressure sensor at the tip end.

If a shape or a material (that is, Young's modulus) of linear body 1 is different, the degree of bending of linear body 1 is different even when the same compressive force is applied. Therefore, if a plurality of linear bodies 1 different in shape or material are used, correlation between the degree of bending of linear body 1 to be used and compressive force in the direction of longitudinal axis applied to linear body 1 is determined in advance and stored in conversion circuit 12. The measurement device also includes a selector 13 shown in FIG. 5, which selects which correlation is to be used, in accordance with linear body 1 that is used. Thus, as the same measurement device is applicable to linear bodies 1 of various shapes or materials, linear bodies 1 that have been used for various different applications so far can be used without modification, and cost effectiveness is achieved.

Figure 8:
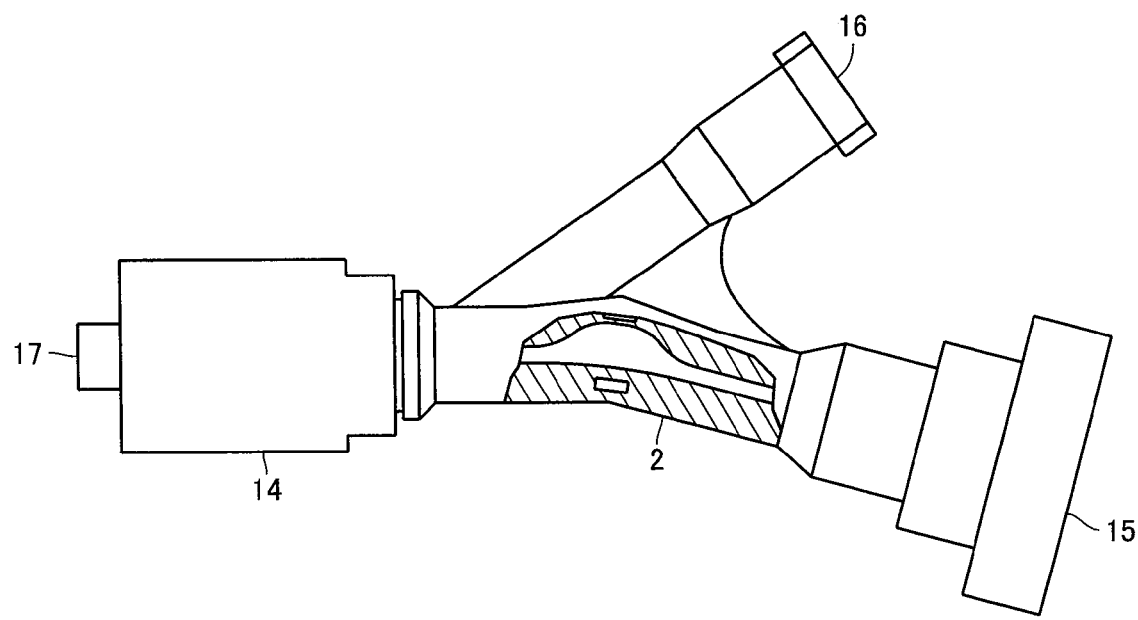
FIG. 8 is a schematic diagram showing an example of incorporation for use in a Y-connector.

Incorporation for use in other medical equipment, of the measurement device measuring compressive force in the direction of longitudinal axis applied to the linear body representing a linear medical appliance to be inserted in a vessel in a body is shown as an example of practical use of the measurement device according to the present invention. FIG. 8 is a schematic diagram showing an example where measurement device main body 2 is incorporated for use in a Y-connector 14. In FIG. 8, Y-connector 14 includes an input port 15, another input port 16, and an output port 17. Measurement device 2 is incorporated in a passage communicating between input port 15 and output port 17 within Y-connector 14. Linear body 1 is a linear medical appliance such as a guide wire or a catheter inserted in a vessel in a body such as a blood vessel and a ureter, or a wire having an embolus coil attached at a tip end for embolizing an aneurysm, and it is guided to a destination in the body through an operation from the input port 15 side.

By thus measuring increase in compressive force in the direction of longitudinal axis applied to the linear medical appliance inserted in the vessel in the body, load applied to the vessel in the body by the medical appliance can be measured as reaction force against compressive force. Namely, contact of the tip end of the medical appliance with the inner wall of the vessel can be sensed. Therefore, application of excessive load onto the vessel in the body can be prevented. In addition, as the measurement device according to the present invention is incorporated in Y-connector 14, the linear medical appliance is operated through input port 15 of Y-connector 14 while a medicine can be injected through another input port 16. For example, physiological saline for reducing friction between the catheter and the guide wire can be injected through another input port 16. In addition, for example, after the catheter inserted in the blood vessel is guided from the outside of a human body to the destination, a contrast medium can be injected through another input port 16 so that the contrast medium can reach the destination in the body.

A method of outputting compressive force obtained by the measurement device according to the present invention will now be described. There are some methods, and a representative method includes a visualizing instrument displaying compressive force obtained by converting the output detected by sensor 7 in a numeric value, on a meter, or in a graph, and an auralizing instrument converting variation in the output of the sensor into voice and sound. The measurement device may include any one of the visualizing instrument and the auralizing instrument, or may include both of them.

Figure 9:
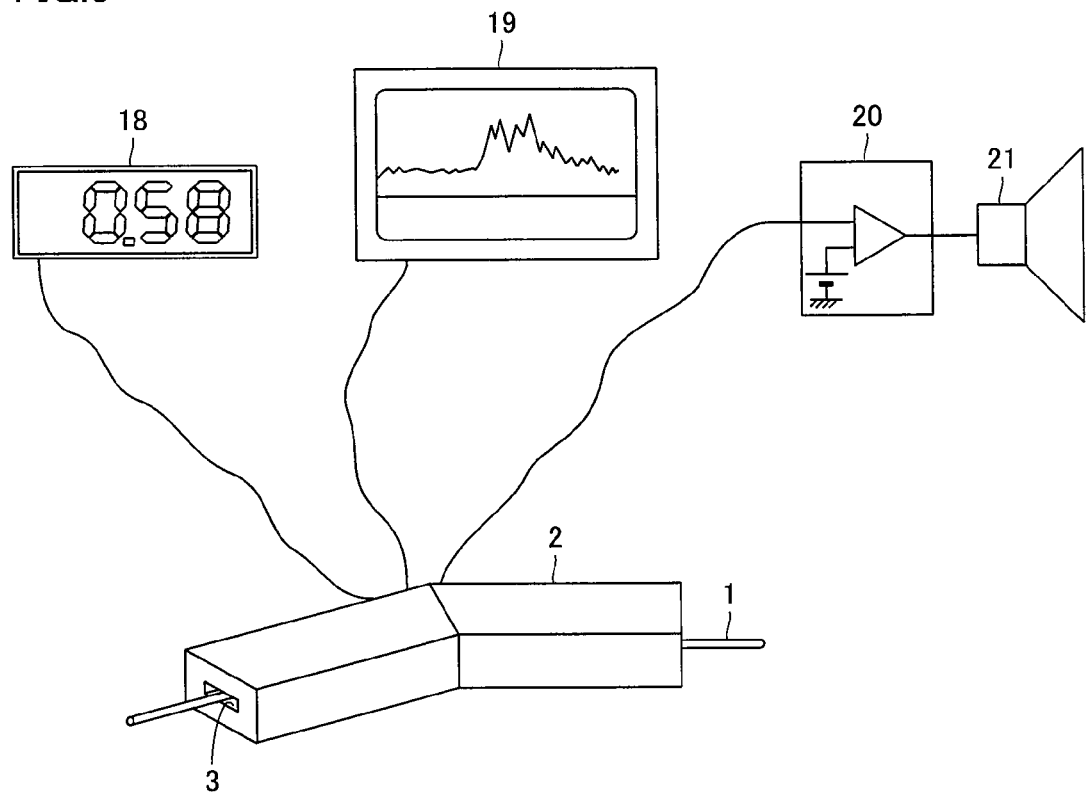
FIG. 9 is a schematic diagram showing an example of an output method in the measurement device.

FIG. 9 is a schematic diagram showing an example of the output method in the measurement device. FIG. 9 illustrates a visualizing instrument 18 displaying a numeric value obtained by converting a voltage output of sensor 7 into compressive force applied to linear body 1 and a visualizing instrument 19 displaying compressive force in a graph together with time history. In addition, FIG. 9 illustrates an auralizing instrument 20 varying a sound effect, that is, sounding an alarm from a speaker 21 when the voltage output of the sensor is equal to or greater than a prescribed threshold value determined in advance, that is, when compressive force applied to linear body 1 is equal to or greater than a prescribed threshold value. The fact that compressive force applied to linear body 1 is equal to or greater than the prescribed threshold value can be indicated also by varying a visual effect such as illumination of an indicator. Alternatively, the speaker and the indicator may together be used. Further, a plurality of threshold values are determined in advance, and the sound from the speaker or a color of the indicator may be changed when each threshold value is reached. As sudden change in the visual effect or the sound effect on reaching the threshold value can reliably draw the attention of the operator, it is effective. For example, on reaching the threshold value, the color of light emission from the indicator may be changed or the sound of the alarm (discontinuous sound and continuous sound, low pitch sound and high pitch sound, and the like) may be changed. In FIG. 9, though measurement device main body 2 is connected to visualizing instrument 18, visualizing instrument 19, and auralizing instrument 20 through a cable, other signal transfer means such as wireless communication through infrared or other electromagnetic waves may also be employed.

Thus, kinesthetic sense information of insertion resistance of linear body 1 externally held with fingers of the operator can be quantified and displayed. In addition, the kinesthetic sense information can be recorded as data, for example as a matter printed on paper in a graph or a numeric value or as electronic data in a hard disk or a memory. Therefore, manipulation of the skilled operator can quantitatively be transferred to the less experienced operator. Moreover, the operator can reliably recognize the time when compressive force applied to linear body 1 is equal to or greater than the threshold value determined in advance through the alarm or illumination of the indicator. Therefore, application of excessive load onto the vessel can be prevented.

Figure 10:
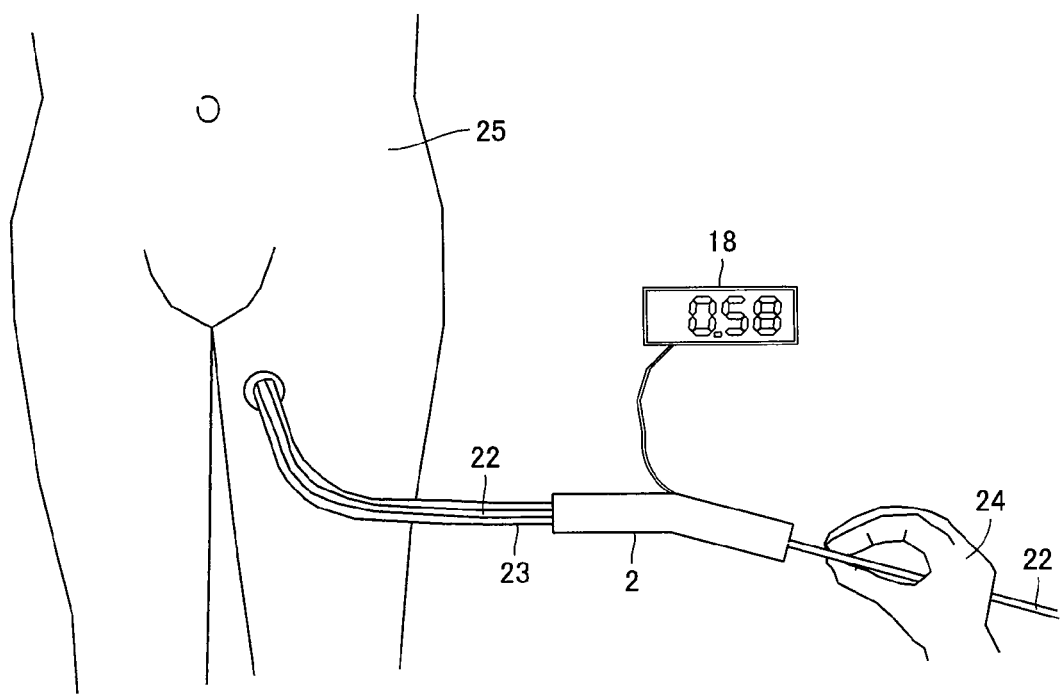
FIG. 10 is a schematic diagram showing an example where the measurement device is used with a linear medical appliance to be inserted in a vessel in a human body.

An example where the measurement device according to the present invention is used in actual medical practice such as treatment or examination will now be described. FIG. 10 is a schematic diagram showing an example where the measurement device is used with a linear medical appliance to be inserted in a vessel in a human body. In FIG. 10, a catheter 23 is connected to measurement device main body 2, and guide wire 22 passing through through hole 3 in measurement device main body 2 is located in catheter 23. In addition, catheter 23 is inserted in the vessel in a human body 25. If there is insertion resistance against the vessel in human body 25 when an operator 24 holding guide wire 22 applies force in the direction of longitudinal axis to guide wire 22 in order to advance guide wire 22 into the body, compressive force is applied to guide wire 22 in the direction of longitudinal axis. This compressive force is displayed by visualizing instrument 18.

Figure 11:
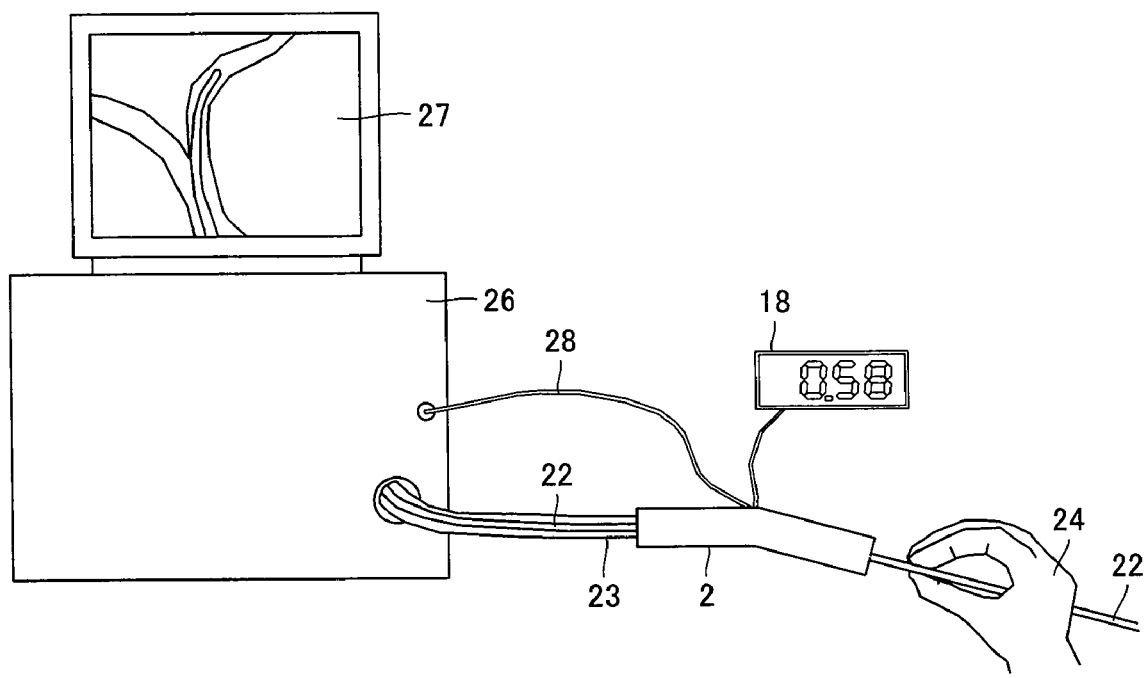
FIG. 11 is a schematic diagram showing an example where the measurement device is attached to a training simulator simulating a human body for use.

FIG. 11 is a schematic diagram showing an example where the measurement device is attached to a training simulator simulating a human body for use. In FIG. 11, a simulator 26 displays a simulated perspective image 27 equivalent to a perspective image of a vessel in a human body in which a linear medical appliance is inserted. Operator 24 in training operates guide wire 22 while viewing simulated perspective image 27. Simulator 26 varies the insertion resistance of inserted guide wire 22. Resistance during operation, i.e., compressive force applied to guide wire 22 that is measured by the measurement device, is displayed on visualizing instrument 18 and also transmitted to simulator 26 through a cable 28, thus contributing to change in the insertion resistance of guide wire 22 in simulator 26. Though measurement device main body 2 is separate from simulator 26 in FIG. 11, measurement device main body 2 may integrally be incorporated in simulator 26. Alternatively, instead of including visualizing instrument 18, compressive force applied to guide wire 22 may be displayed in simulated perspective image 27 of simulator 26.

Thus, manipulation of the skilled operator can be quantified and manipulation can quantitatively be transferred to the less experienced operator. Therefore, manipulation of the less experienced operator can quickly be improved.

Embodiment 2

Figure 12:
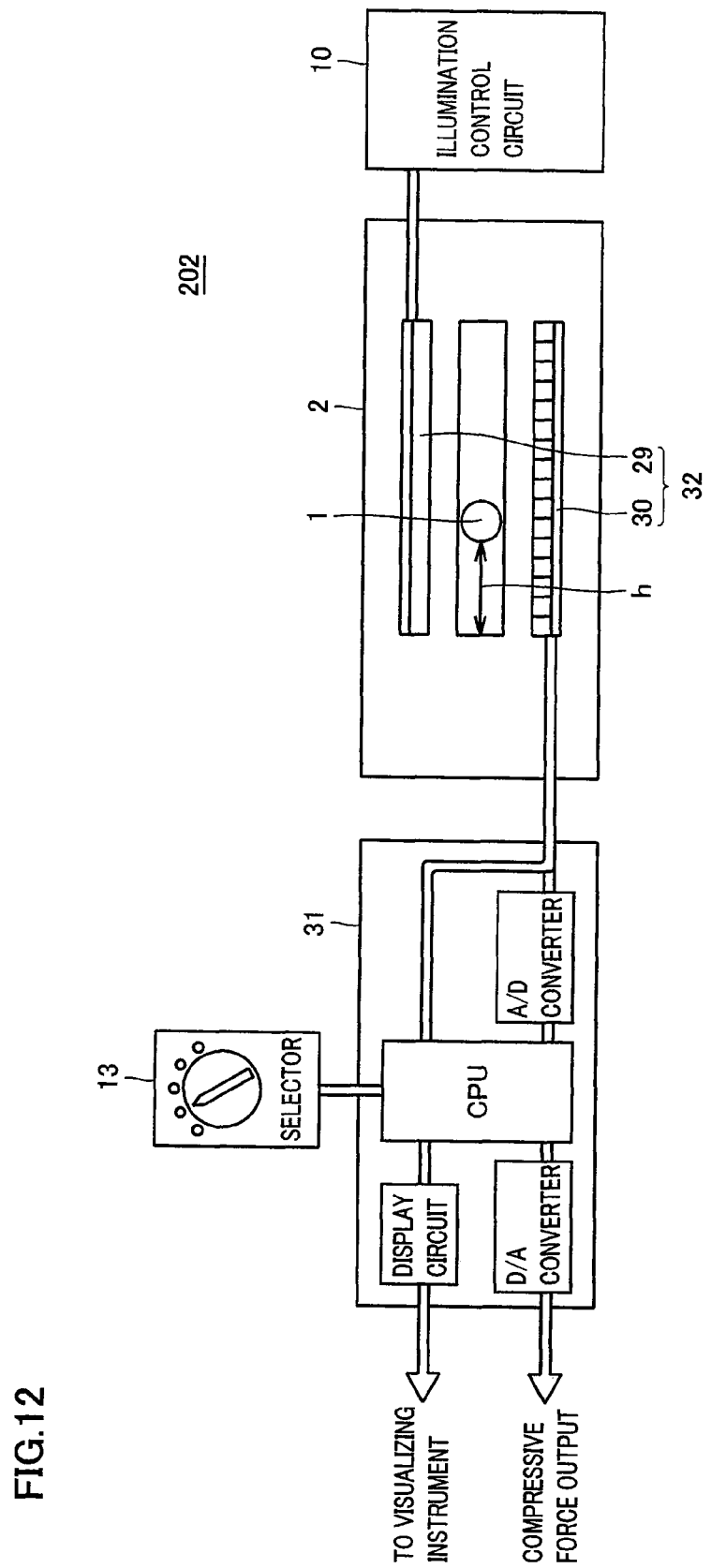
FIG. 12 is a schematic diagram showing an overall configuration of a measurement device according to Embodiment 2 of the present invention.
Figure 13:
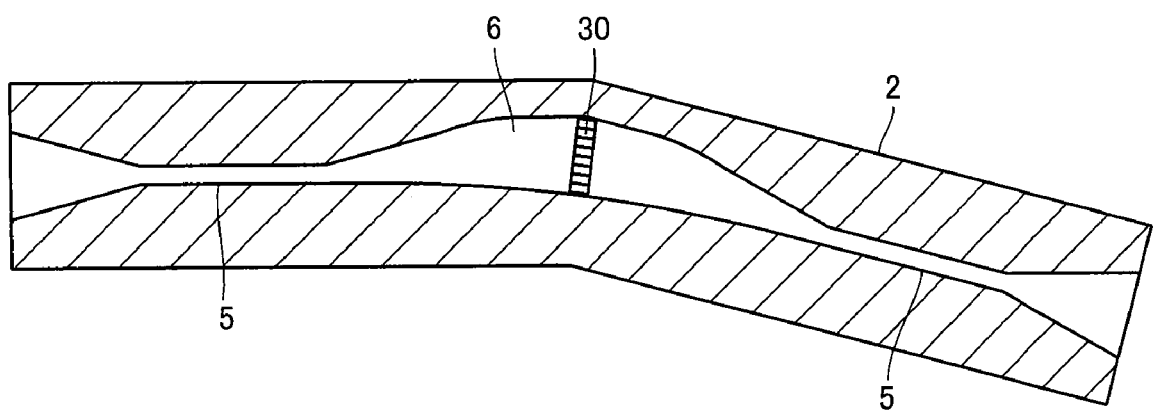
FIG. 13 is a cross-sectional schematic diagram showing an internal structure of a main body of the measurement device shown in FIG. 12.

FIG. 12 is a schematic diagram showing an overall configuration of a measurement device according to Embodiment 2 representing one embodiment of the present invention. FIG. 13 is a cross-sectional schematic diagram showing an internal structure of a main body of the measurement device shown in FIG. 12. The measurement device in Embodiment 2 is basically configured in a manner similar to the measurement device in Embodiment 1 described above. Embodiment 2, however, is different from Embodiment 1 in that the sensor is configured as shown in FIG. 12.

Specifically, in FIG. 12, a measurement device 202 includes an optical sensor 32 instead of sensor 7. Optical sensor 32 includes a light source 29 emitting light and a light receiver 30 receiving light emitted by light source 29. Light receiver 30 is a line sensor representing a one-dimensional optical array sensor, that has a plurality of light-receiving elements receiving light arranged in line. In FIG. 13, light receiver 30 is arranged in a direction of height of the peak of bending, that is formed by bending of linear body 1 when compressive force in the direction of longitudinal axis is applied to linear body 1, in space 6 within measurement device main body 2. Namely, not-shown light source 29 and light receiver 30 are arranged to be opposed to each other with linear body 1 lying therebetween, across space 6 formed between two restraint portions 5, and arranged along a direction intersecting the direction of longitudinal axis of linear body 1 and in a direction the same as a direction of bending of linear body 1 when compressive force in the direction of longitudinal axis is applied to linear body 1.

An operation of the measurement device in Embodiment 2 will now be described. The measurement device in Embodiment 2 operates basically in a manner the same as the measurement device in Embodiment 1 described above. In the measurement device in Embodiment 2, however, when light receiver 30 receives light emitted by light source 29, linear body 1 is located over a certain light-receiving element in the line sensor serving as light receiver 30 and it cuts off light emitted by light source 29, and therefore the quantity of light received by the light-receiving element decreases. By detecting a position of that light-receiving element, a position of linear body 1 can be detected and the degree of bending of linear body 1 can be detected. Namely, a compressive force output device 31 shown in FIG. 12 can detect the degree of bending of linear body 1 based on an output of each light-receiving element of light receiver 30. Then, the degree of bending of linear body 1 can be converted into compressive force applied to linear body 1 for output, based on predetermined correlation between the degree of bending of linear body 1 and compressive force applied to linear body 1. In order to appropriately form an image of linear body 1 over light receiver 30, an optical element such as a lens, a slit, or a filter cutting off outside light may be provided in the present optical system.

Embodiment 3

Figure 14:
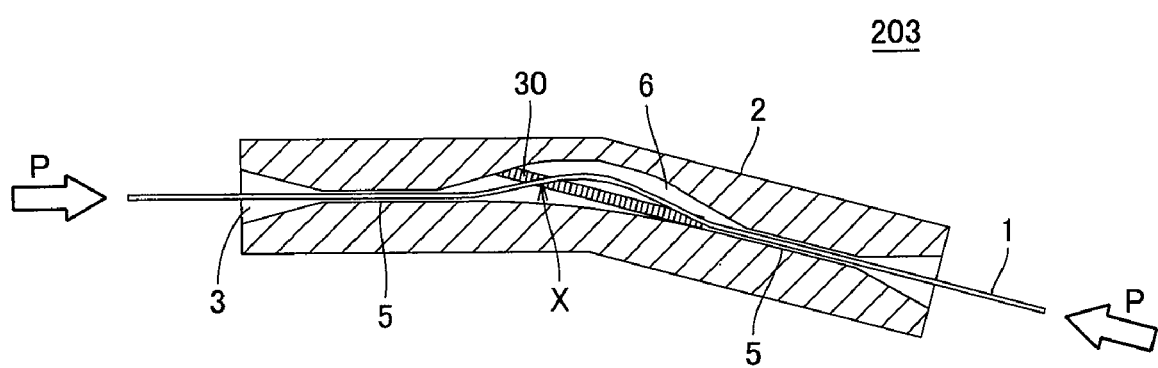
FIG. 14 is a cross-sectional schematic diagram showing an internal structure of a main body of a measurement device according to Embodiment 3 of the present invention.

FIG. 14 is a cross-sectional schematic diagram showing an internal structure of a main body of a measurement device according to Embodiment 3 representing one embodiment of the present invention. A measurement device 203 in Embodiment 3 is basically configured in a manner similar to the measurement device in Embodiment 2 described above.

Embodiment 3, however, is different from Embodiment 2 in that light receiver 30 is arranged as shown in FIG. 14. Specifically, in FIG. 14, the line sensor serving as light receiver 30 is arranged on an extension of one restraint portion 5 in space 6 of through hole 3 curving between two restraint portions 5. Namely, not-shown light source 29 and light receiver 30 are arranged to be opposed to each other with linear body 1 lying therebetween, across space 6 formed between two restraint portions 5, and arranged along a direction in which through hole 3 extends in one restraint portion 5.

An operation of the measurement device in Embodiment 3 will now be described. The measurement device in Embodiment 3 operates basically in a manner the same as the measurement device in Embodiment 2 described above. In the measurement device in Embodiment 3, however, when light receiver 30 receives light emitted by light source 29, linear body 1 is located over a certain light-receiving element in the line sensor serving as light receiver 30 and it cuts off light emitted by light source 29, and therefore the quantity of light received by the light-receiving element decreases. By detecting a position of that light-receiving element, a position X of an intersection of the line sensor serving as light receiver 30 and linear body 1 can be detected. The degree of bending of linear body 1 can be detected based on the position of this intersection, and compressive force applied to linear body 1 can be measured based on predetermined correlation between the degree of bending of linear body 1 and compressive force applied to linear body 1.

In the description above, in connection with the optical sensor, a detection method in which the light receiver arranged at a position opposed to the light source receives transmitted light is described, however, the light source and the light receiver may be arranged side by side and a reflector such as a mirror reflecting light emitted by the light source may be provided at a position opposed to the light source. Here, the light receiver receives light reflected by the reflector, out of light emitted by the light source, so that the degree of bending of the linear body can similarly be detected. Alternatively, instead of the one-dimensional array sensor such as the line sensor, a two-dimensional array sensor, for example, implemented by arranging a plurality of light-receiving elements on a plane in matrix may be used to detect the degree of bending of the linear body. Further, as the degree of bending of the linear body should only be detected, for example, a non-contact distance sensor detecting height h of the peak of bending, a position sensor detecting a position of the linear body, or the like may also be employed.

Embodiment 4

Figure 15:
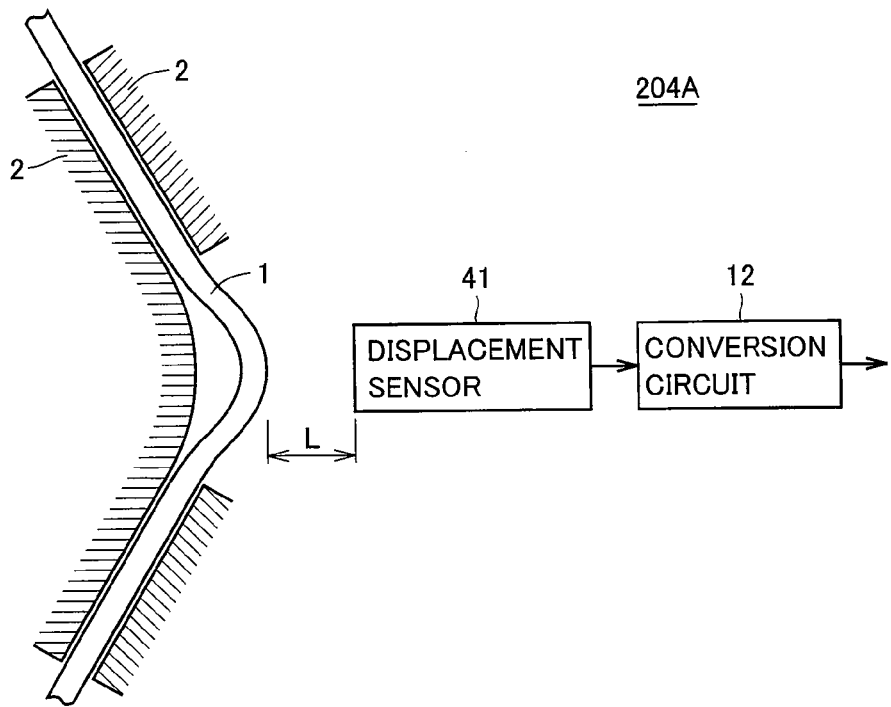
FIG. 15 is a schematic diagram showing a configuration of a measurement device according to Embodiment 4 representing one embodiment of the present invention.

FIG. 15 is a schematic diagram showing a configuration of a measurement device according to Embodiment 4 representing one embodiment of the present invention.

Referring to FIG. 15, a measurement device 204A includes measurement device main body 2, a displacement sensor 41, and conversion circuit 12.

When compressive force P is applied to linear body 1, linear body 1 is bent and height h of the peak of bending increases. Displacement sensor 41 is arranged in a direction of bending of linear body 1.

Displacement sensor 41 detects a distance L between displacement sensor 41 and a bending portion of linear body 1. Detection of distance L is equivalent to measurement of the height of the bending portion, that is, height h of the peak of bending. Conversion circuit 12 stores the result of determination in advance of correlation between compressive force P in the direction of longitudinal axis applied to linear body 1 and distance L, that is, the degree of bending of linear body 1. Conversion circuit 12 converts detected distance L to compressive force P using the stored correlation. Compressive force P in the direction of longitudinal axis applied to linear body 1 can thus be measured.

The measurement device according to the embodiment of the present invention can appropriately adapt to an environment of use, specifications and the like, by including various sensors described below as displacement sensor 41.

Figure 16:
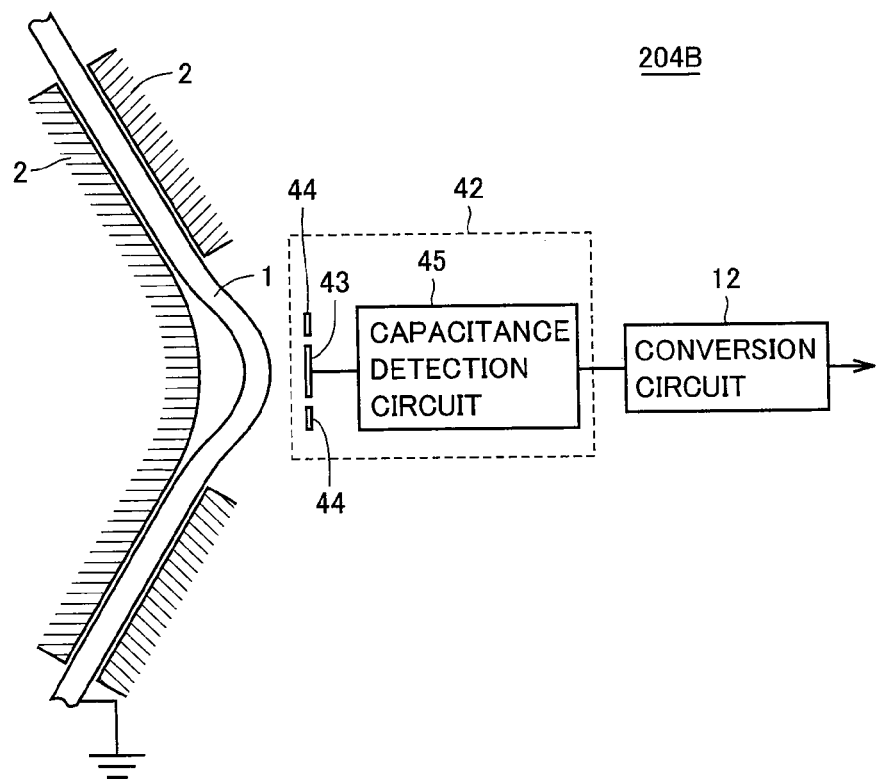
FIG. 16 is a schematic diagram showing a configuration of the measurement device including a capacitance sensor as a displacement sensor, according to Embodiment 4 representing one embodiment of the present invention.

FIG. 16 is a schematic diagram showing a configuration of the measurement device including a capacitance sensor as the displacement sensor, according to Embodiment 4 representing one embodiment of the present invention.

Referring to FIG. 16, a measurement device 204B includes measurement device main body 2, a capacitance sensor 42, and conversion circuit 12. Capacitance sensor 42 includes a detection electrode 43, a guard electrode 44, and a capacitance detection circuit 45.

Capacitance detection circuit 45 detects displacement in a distance between detection electrode 43 and linear body 1 as variation in the capacitance. Namely, the capacitance generated between detection electrode 43 and linear body 1 varies in accordance with distance L between detection electrode 43 and linear body 1. Capacitance detection circuit 45 detects the capacitance between detection electrode 43 and linear body 1 and detects the degree of bending of linear body 1 based on the detected capacitance. Guard electrode 44 is provided in order to protect electric field between detection electrode 43 and linear body 1.

Conversion circuit 12 stores the result of determination in advance of correlation between compressive force P in the direction of longitudinal axis applied to linear body 1 and the capacitance. Then, conversion circuit 12 converts the capacitance detected by capacitance detection circuit 45 to an electric signal indicating compressive force P for output.

According to such a configuration, adaptation to a measurement device in which high resolution or high frequency response is required can be achieved. In addition, unlike the optical sensor, compressive force P can accurately be measured even though linear body 1 is transparent.

Embodiment 5

Figure 17:
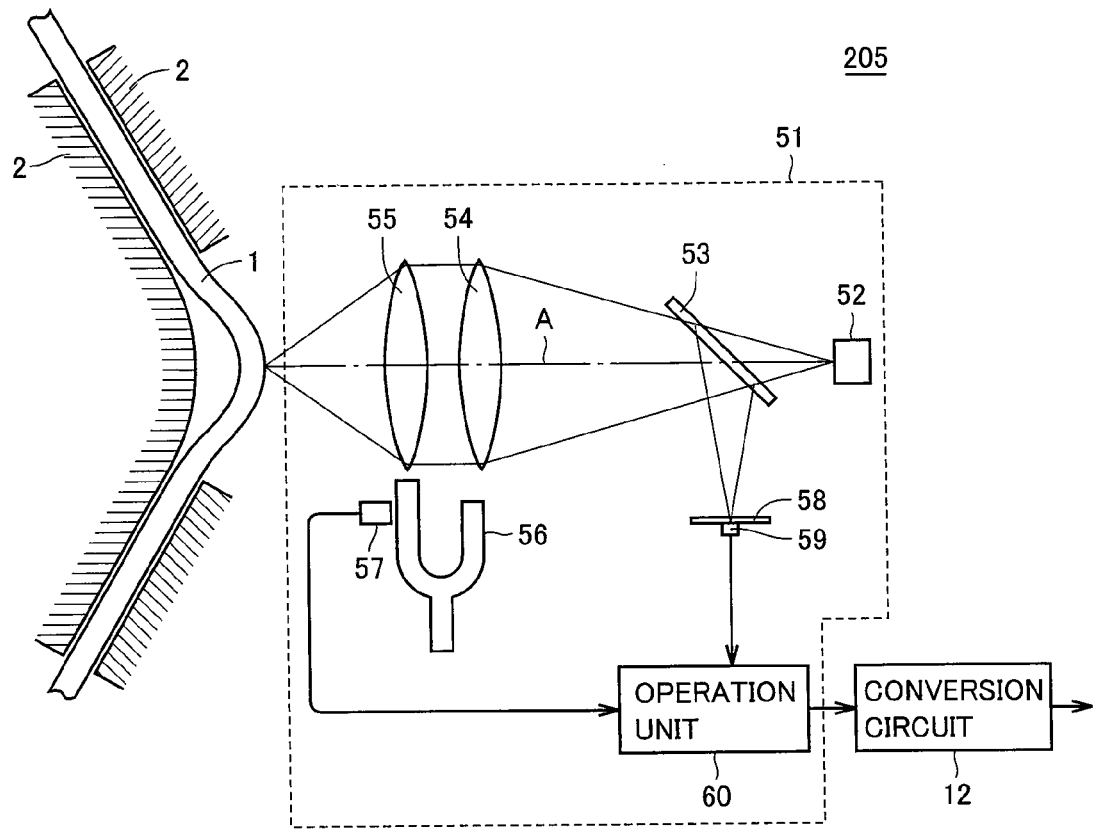
FIG. 17 is a schematic diagram showing a configuration of a measurement device according to Embodiment 5 representing one embodiment of the present invention.

FIG. 17 is a schematic diagram showing a configuration of a measurement device according to Embodiment 5 representing one embodiment of the present invention.

Referring to FIG. 17, a measurement device 205 includes measurement device main body 2, an optical sensor 51, and conversion circuit 12. Optical sensor 51 includes a semiconductor laser (light source) 52, a half mirror 53, a collimating lens 54, an objective lens 55, a tuning fork (moving portion) 56, a tuning fork position detection unit (objective lens position detection unit) 57, a pinhole 58, a light-receiving element (light receiver) 59, and an operation unit 60.

Semiconductor laser 52 outputs a laser beam. The laser beam output from semiconductor laser 52 passes through half mirror 53 and is directed to collimating lens 54. Collimating lens 54 converts the incident laser beam into parallel light, which is in turn directed to objective lens 55. Objective lens 55 refracts the emitted parallel light, which is in turn directed to linear body 1.

When the laser beam directed from objective lens 55 is focused on a surface of linear body 1, a part of the laser beam reflected by linear body 1 passes through objective lens 55 and collimating lens 54 to reach half mirror 53. Here, out of the laser beam reflected by linear body 1, the light reflected at the surface of the linear body substantially perpendicular to an optical axis A extending mainly in a direction of the parallel light from collimating lens 54 is directed to objective lens 55. Half mirror 53 refracts the incident laser beam to the light-receiving element 59 side, which is in turn directed to light-receiving element 59 through pinhole 58.

When the laser beam directed from objective lens 55 is not focused on the surface of linear body 1, light reflected by linear body 1 toward objective lens 55 is less. In addition, as pinhole 58 exists, there is almost no laser beam that reaches light-receiving element 59 from linear body 1.

Objective lens 55 is coupled to tuning fork 56 and vibrates in the direction of optical axis A in accordance with vibration of tuning fork 56. When objective lens 55 moves in the direction of optical axis A, the position of focus of the laser beam from objective lens 55 moves in the direction of optical axis A.

Light-receiving element 59 converts the laser beam that has passed through pinhole 58 into an electric signal. Here, light-receiving element 59 generates an electric signal having a level in accordance with a quantity of received light.

Tuning fork position detection unit 57 detects a position of tuning fork 56, that is, a position of objective lens 55, and outputs an objective lens position signal indicating the result of detection.

When the laser beam directed from objective lens 55 is focused on the surface of linear body 1, the quantity of light received by light-receiving element 59 is maximized. Therefore, operation unit 60 detects a position of a reflection surface of linear body 1, that is, the degree of bending of linear body 1, based on the position of objective lens 55 indicated by the objective lens position signal when the quantity of light received by light-receiving element 59 is maximized.

Conversion circuit 12 stores the result of determination in advance of correlation between compressive force P in the direction of longitudinal axis applied to linear body 1 and the objective lens position signal. Then, conversion circuit 12 converts the degree of bending of linear body 1 detected by operation unit 60 to an electric signal indicating compressive force P for output.

According to such a configuration, adaptation to a measurement device in which high resolution is required can be achieved.

Embodiment 6

Figure 18:
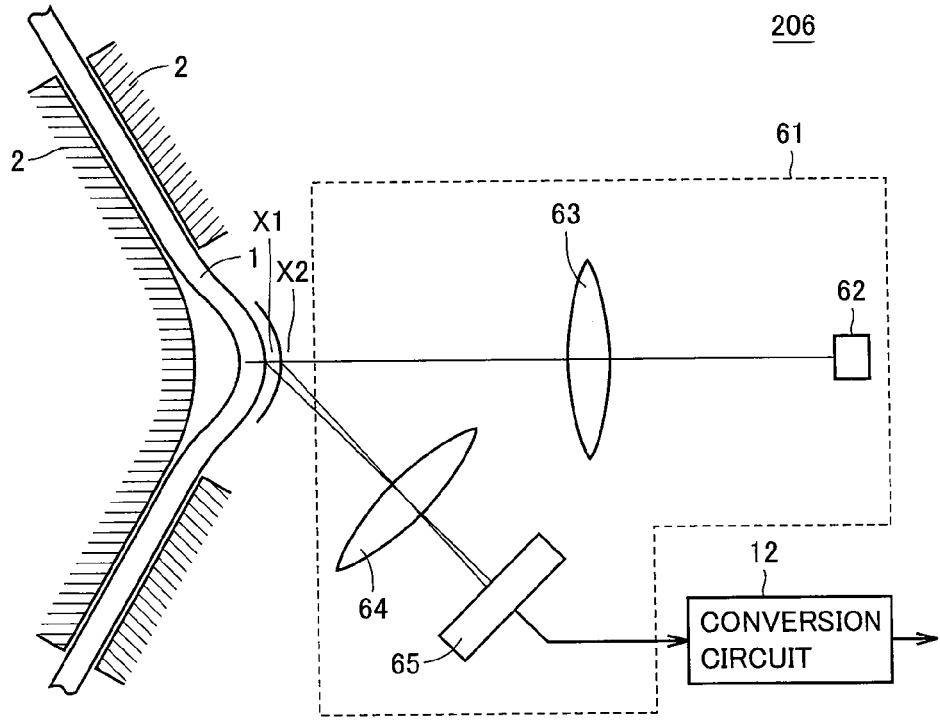
FIG. 18 is a schematic diagram showing a configuration of a measurement device according to Embodiment 6 representing one embodiment of the present invention.

FIG. 18 is a schematic diagram showing a configuration of a measurement device according to Embodiment 6 representing one embodiment of the present invention.

Referring to FIG. 18, a measurement device 206 includes measurement device main body 2, an optical sensor 61, and conversion circuit 12. Optical sensor 61 includes a semiconductor laser (light source) 62, a light-transmissive lens 63, a light-receiving lens 64, and an image processing unit 65.

Semiconductor laser 62 outputs a laser beam. Light-transmissive lens 63 directs the laser beam output from semiconductor laser 62 to linear body 1. Light-receiving lens 64 directs the laser beam reflected by linear body 1 to image processing unit 65.

Image processing unit 65 picks up an image of linear body 1 based on the laser beam directed from light-receiving lens 64. Here, when linear body 1 moves from a position X1 to a position X2, the image picked up by image processing unit 65 moves, because an angle of reflection of the reflected light when viewed from light-receiving lens 64 is different. Therefore, image processing unit 65 can detect the degree of bending of linear body 1 based on the image of linear body 1. For example, image processing unit 65 detects a position of center of gravity of the image of linear body 1 and detects the degree of bending of linear body 1. In addition, if image processing unit 65 is implemented by a line sensor, it detects the degree of bending of linear body 1 based on variation in a position of the image of linear body 1.

Conversion circuit 12 converts the degree of bending of linear body 1 detected by image processing unit 65 into an electric signal indicating compressive force P for output.

According to such a configuration, adaptation to a measurement device in which high resolution or high frequency response is required can be achieved.

Embodiment 7

Figure 19:
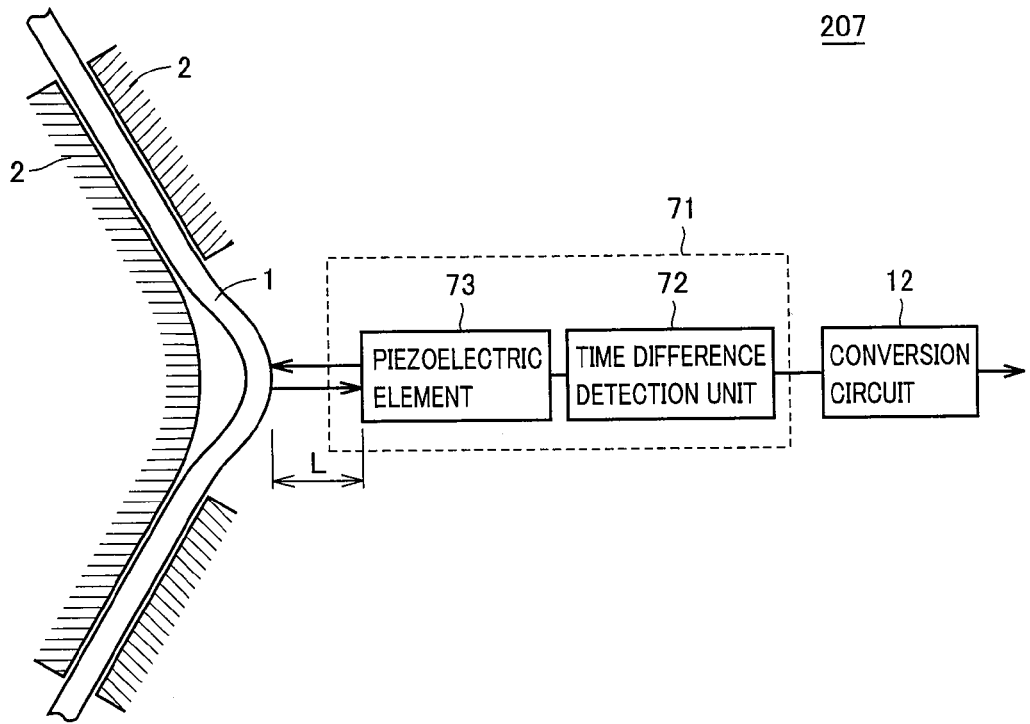
FIG. 19 is a schematic diagram showing a configuration of a measurement device according to Embodiment 7 representing one embodiment of the present invention.

FIG. 19 is a schematic diagram showing a configuration of a measurement device according to Embodiment 7 representing one embodiment of the present invention.

Referring to FIG. 19, a measurement device 207 includes measurement device main body 2, an ultrasonic sensor 71, and conversion circuit 12. Ultrasonic sensor 71 includes a time difference detection unit 72 and a piezoelectric element 73.

Piezoelectric element 73 outputs pulse-like ultrasound to linear body 1 based on an alternating-current voltage supplied from a not-shown power supply circuit or time difference detection unit 72. In addition, piezoelectric element 73 receives ultrasound reflected by linear body 1. Piezoelectric element 73 may include a piezoelectric element for transmitting ultrasound and a piezoelectric element for receiving ultrasound, or it may be implemented by a piezoelectric element for transmitting and receiving ultrasound.

Time difference detection unit 72 detects a time period from output of the pulse-like ultrasound by piezoelectric element 73 to linear body 1 until reception of the pulse-like ultrasound reflected by linear body 1 and detects distance L between piezoelectric element 73 and the bending portion of linear body 1, that is, the degree of bending of linear body 1, based on the detected time period.

Conversion circuit 12 converts the degree of bending of linear body 1 detected by time difference detection unit 72 to an electric signal indicating compressive force P for output.

According to such a configuration, unlike the optical sensor, compressive force P can accurately be measured even though linear body 1 is transparent.

Embodiment 8

Figure 20:
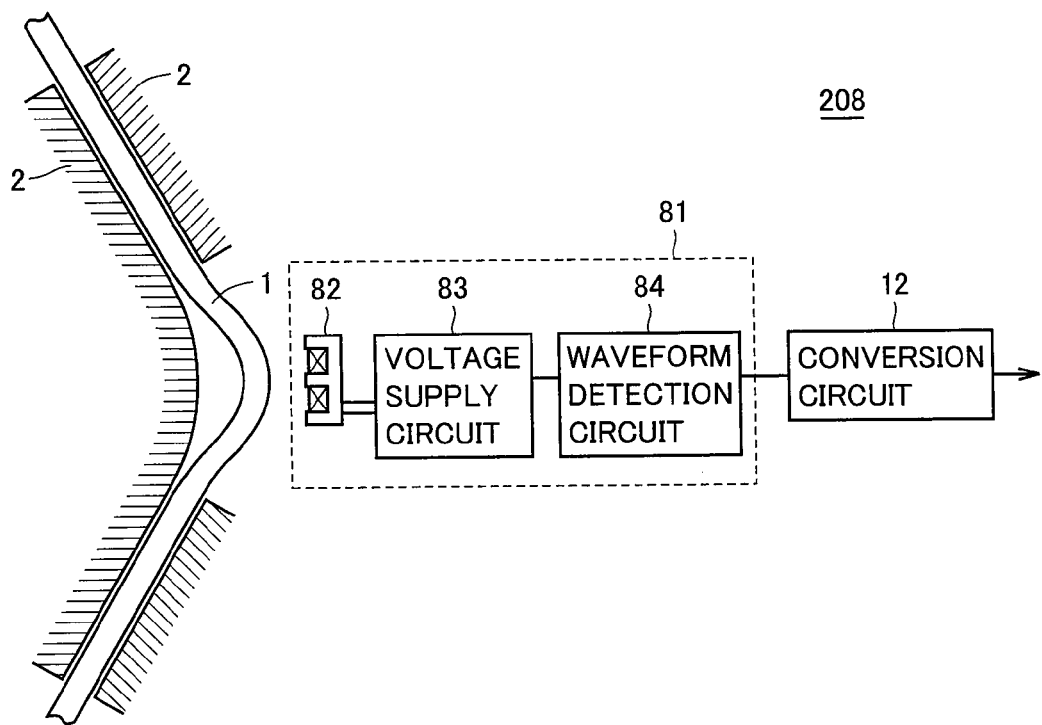
FIG. 20 is a schematic diagram showing a configuration of a measurement device according to Embodiment 8 representing one embodiment of the present invention.

FIG. 20 is a schematic diagram showing a configuration of a measurement device according to Embodiment 8 representing one embodiment of the present invention.

Referring to FIG. 20, a measurement device 208 includes measurement device main body 2, an eddy current sensor 81, and conversion circuit 12. Eddy current sensor 81 includes a detection coil 82, a voltage supply circuit 83, and a waveform detection circuit 84. In the present embodiment, linear body 1 is a conductor.

A high-frequency current flows through detection coil 82 based on a high-frequency voltage supplied from voltage supply circuit 83. Then, high-frequency magnetic field is generated by detection coil 82. Here, since linear body 1 is a conductor, as linear body 1 and detection coil 82 are closer to each other, an eddy current flows over the surface of linear body 1 as a result of electromagnetic induction, and inductance of detection coil 82 is varied. The eddy current generated over the surface of linear body 1 generates magnetic flux in a direction preventing the flow of magnetic flux generated from detection coil 82.

When the inductance of detection coil 82 varies, a waveform of the current that flows through detection coil 82 varies. More specifically, an amplitude of the waveform of the current that flows through detection coil 82 and a phase difference between a waveform of the voltage supplied to detection coil 82 and the waveform of the current that flows through detection coil 82 vary.

Waveform detection circuit 84 detects the amplitude of the waveform of the current that flows through detection coil 82 or the phase difference between the waveform of the voltage supplied to detection coil 82 and the waveform of the current that flows through detection coil 82, and detects the degree of bending of linear body 1 based on the result of detection.

Conversion circuit 12 converts the degree of bending of linear body 1 detected by waveform detection circuit 84 to an electric signal indicating compressive force P for output.

According to such a configuration, adaptation to a measurement device in which high resolution or high frequency response is required can be achieved. In addition, unlike the optical sensor, compressive force P can accurately be measured even though the measurement device is used in an adverse environment such as in the water and in the oil.

Embodiment 9

Figure 21:
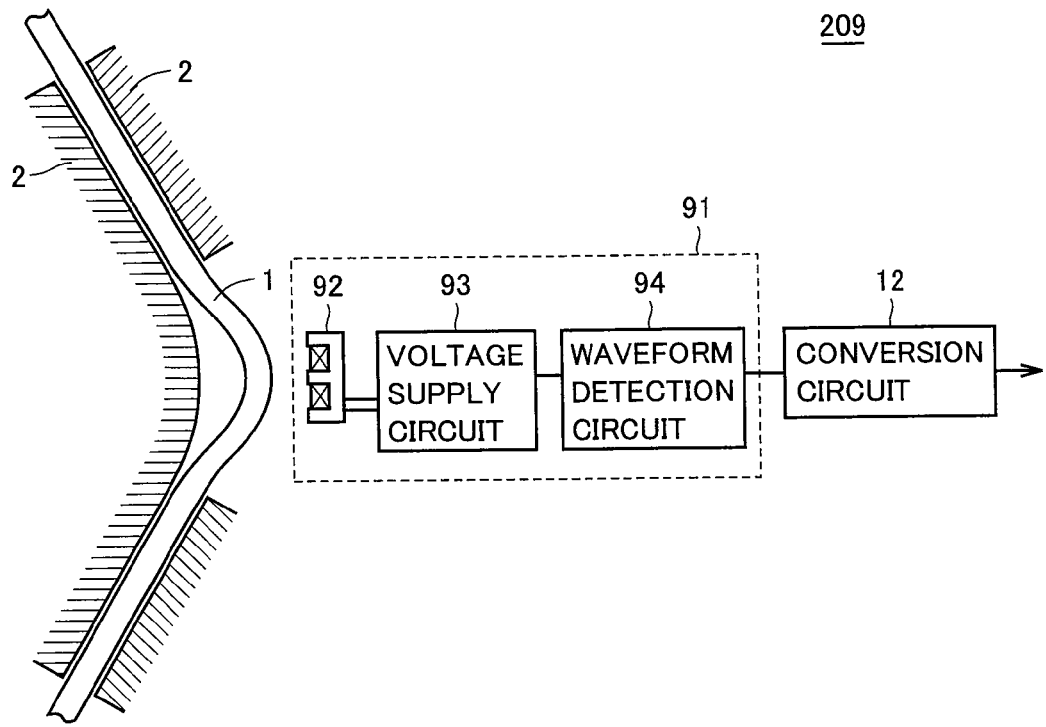
FIG. 21 is a schematic diagram showing a configuration of a measurement device according to Embodiment 9 representing one embodiment of the present invention.

FIG. 21 is a schematic diagram showing a configuration of a measurement device according to Embodiment 9 representing one embodiment of the present invention.

Referring to FIG. 21, a measurement device 209 includes measurement device main body 2, a magnetic sensor 91, and conversion circuit 12. Magnetic sensor 91 includes a detection coil 92, a voltage supply circuit 93, and a waveform detection circuit 94. In the present embodiment, linear body 1 is a magnetic element.

A low-frequency current flows through detection coil 92 based on a low-frequency voltage supplied from voltage supply circuit 93. Then, low-frequency magnetic field is generated by detection coil 92. Here, as linear body 1 is a magnetic element, magnetic reluctance of detection coil 92 varies in accordance with a distance between linear body 1 and detection coil 92, that is, the degree of bending of linear body 1.

When the magnetic reluctance of detection coil 92 varies, a waveform of the current that flows through detection coil 92 varies. More specifically, an amplitude of the waveform of the current that flows through detection coil 92 and a phase difference between a waveform of the voltage supplied to detection coil 92 and the waveform of the current that flows through detection coil 92 vary. For example, as linear body 1 and detection coil 92 are closer to each other, magnetic flux passes more easily and magnetic reluctance of detection coil 92 becomes smaller. Then, as the inductance of detection coil 92 becomes greater, the amplitude of the waveform of the current that flows through detection coil 92 becomes smaller and the phase difference between the waveform of the voltage supplied to detection coil 92 and the waveform of the current that flows through detection coil 92 is greater.

Waveform detection circuit 94 detects the amplitude of the waveform of the current that flows through detection coil 92 or the phase difference between the waveform of the voltage supplied to detection coil 92 and the waveform of the current that flows through detection coil 92, and detects the degree of bending of linear body 1 based on the result of detection.

Conversion circuit 12 converts the degree of bending of linear body 1 detected by waveform detection circuit 94 to an electric signal indicating compressive force P for output.

According to such a configuration, unlike the optical sensor, compressive force P can accurately be measured even though the measurement device is used in an adverse environment such as in the water and in the oil.

Embodiment 10

Figure 22:
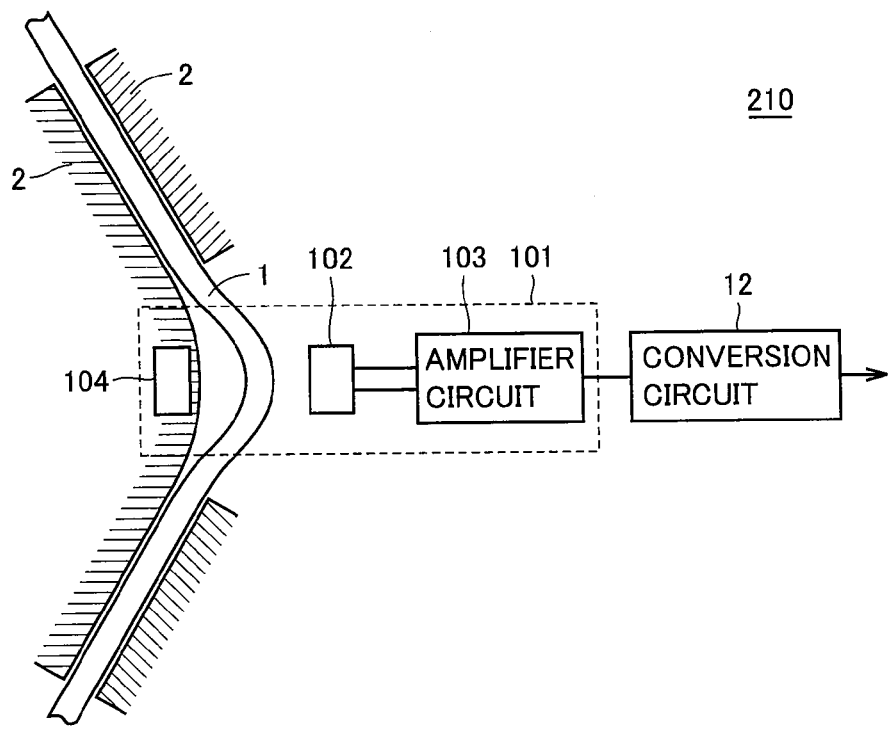
FIG. 22 is a schematic diagram showing a configuration of a measurement device according to Embodiment 10 representing one embodiment of the present invention.

FIG. 22 is a schematic diagram showing a configuration of a measurement device according to Embodiment 10 representing one embodiment of the present invention.

Referring to FIG. 22, a measurement device 210 includes measurement device main body 2, a magnetic sensor 101, and conversion circuit 12. Magnetic sensor 101 includes a Hall sensor (magnetic detection unit) 102, an amplifier circuit 103, and a permanent magnet 104. In the present embodiment, linear body 1 is a magnetic element. It is noted that other magnetic sensors such as an MR sensor may be employed instead of the Hall sensor. In addition, an electromagnet may be employed instead of permanent magnet 104.

Hall sensor 102 detects magnetic flux generated by permanent magnet 104. Magnetic flux from permanent magnet 104 varies in accordance with the degree of bending of linear body 1. Therefore, Hall sensor 102 detects the degree of bending of linear body 1 based on the detected magnetic flux from permanent magnet 104. Amplifier circuit 103 amplifies a signal indicating the result of detection by Hall sensor 102 and outputs the resultant signal to conversion circuit 12.

Conversion circuit 12 converts the degree of bending of linear body 1 detected by Hall sensor 102 to an electric signal indicating compressive force P for output.

According to such a configuration, adaptation to a measurement device in which high frequency response is required can be achieved. In addition, unlike the optical sensor, compressive force P can accurately be measured even though the measurement device is used in an adverse environment such as in the water and in the oil.

Embodiment 11

Figure 23:
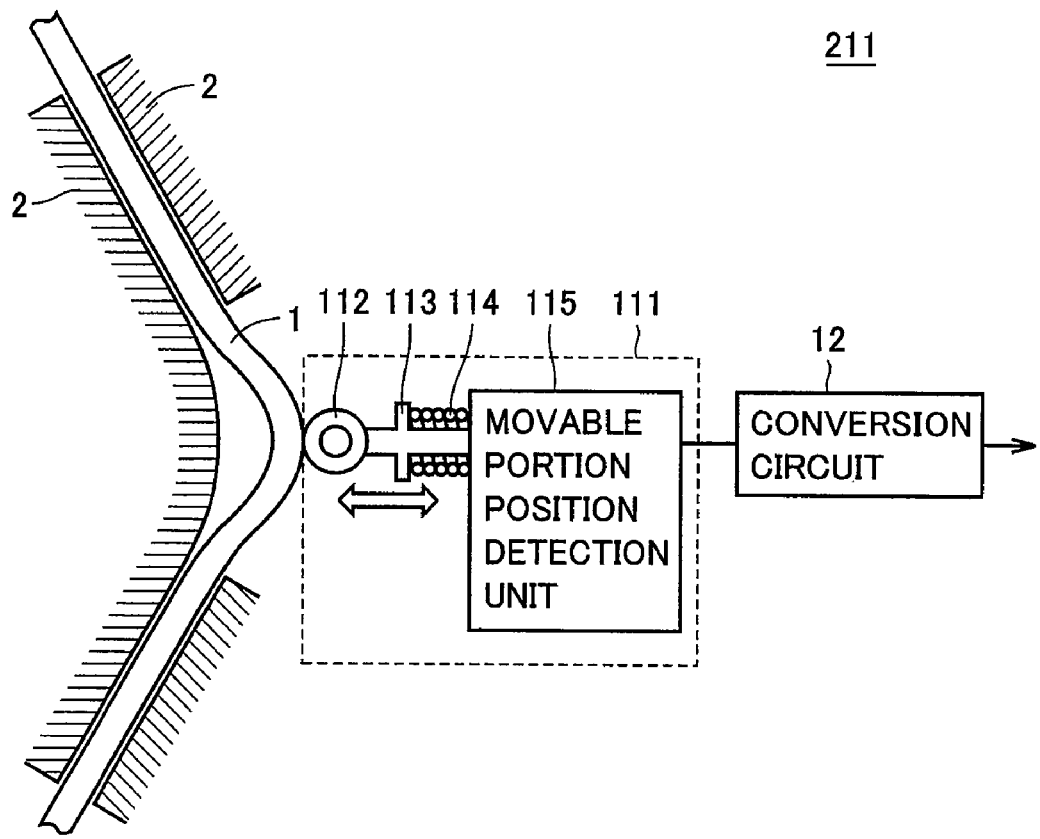
FIG. 23 is a schematic diagram showing a configuration of a measurement device according to Embodiment 11 representing one embodiment of the present invention.

FIG. 23 is a schematic diagram showing a configuration of a measurement device according to Embodiment 11 representing one embodiment of the present invention.

Referring to FIG. 23, a measurement device 211 includes measurement device main body 2, a contact sensor 111, and conversion circuit 12. Contact sensor 111 includes a pulley 112, a stopper 113, a spring 114, and a movable portion position detection unit 115. Pulley 112 and stopper 113 form a movable portion.

Spring 114 couples the movable portion to linear body 1 by constantly pressing pulley 112 against linear body 1 with stopper 113 being interposed. When linear body 1 moves, pulley 112 turns. Therefore, friction between the movable portion and linear body 1 can be prevented. It is noted that a low-friction material coated with Teflon (registered trademark) may be employed instead of the pulley.

Movable portion position detection unit 115 detects a position of the movable portion and detects the degree of bending of linear body 1 based on the result of detection.

Conversion circuit 12 converts the degree of bending of linear body 1 detected by movable portion position detection unit 115 to an electric signal indicating compressive force P for output.

Figure 24:
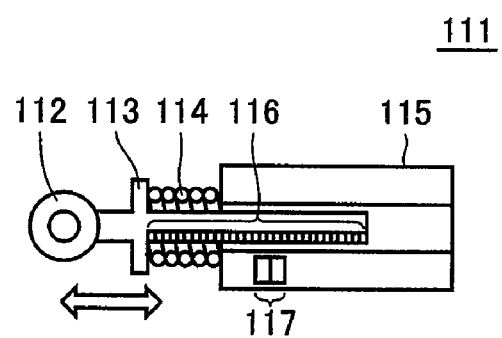
FIG. 24 is a schematic diagram showing a configuration of a contact sensor.

FIG. 24 is a schematic diagram showing a configuration of the contact sensor.

Referring to FIG. 24, contact sensor 111 includes pulley 112, stopper 113, spring 114, and movable portion position detection unit 115. Movable portion position detection unit 115 includes an encoder 116 and an optical sensor 117.

Encoder 116 is configured such that a plurality of substances made of glass or the like different in reflectance are arranged in a direction of movement of the movable portion. Optical sensor 117 detects the position of the movable portion based on light emitted to the movable portion and reflected by encoder 16, and detects the degree of bending of linear body 1 based on the result of detection. For example, in an example where a substance reflecting light toward optical sensor 117 and a substance not reflecting the light are alternately arranged in encoder 116 in the direction of movement of the movable portion, two optical sensors 117 are arranged in the direction of movement of the movable portion at intervals of $\pi/4$, assuming a distance between the substances in encoder 116 in the direction of movement of the movable portion as one cycle. According to such a configuration, the direction of movement of the movable portion can be detected.

It is noted that movable portion position detection unit 115 may be of a magnetic type. Here, encoder 116 is configured such that a substance having magnetic pole N and a substance having magnetic pole S are alternately arranged in the direction of movement of the movable portion. A magnetic sensor 117 arranged instead of optical sensor 117 detects the position of the movable portion based on the magnetic pole of encoder 116 at a prescribed position. Alternatively, movable portion position detection unit 115 may be of a differential transformer type.

Figure 25:
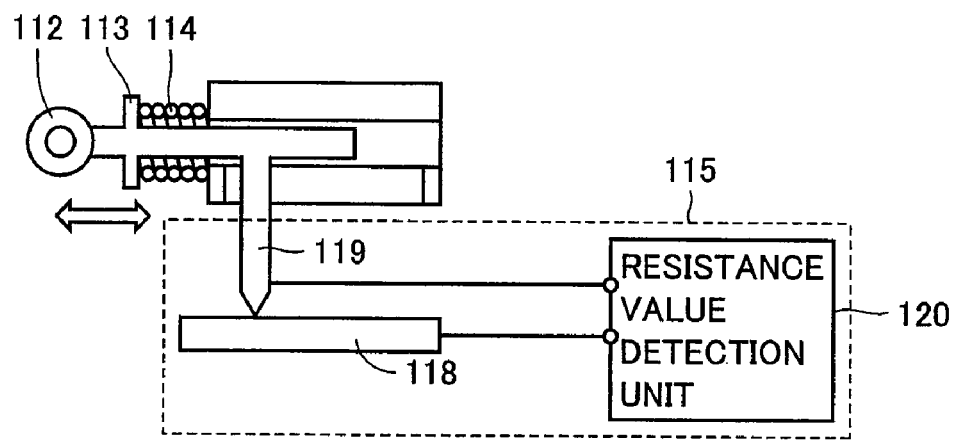
FIG. 25 is a schematic diagram showing another exemplary configuration of the contact sensor.

FIG. 25 is a schematic diagram showing another exemplary configuration of the contact sensor.

Referring to FIG. 25, contact sensor 111 includes pulley 112, stopper 113, spring 114, and movable portion position detection unit 115. Movable portion position detection unit 115 includes a resistor 118, a conductor 119, and a resistance value detection unit 120.

Conductor 119 is attached to stopper 113 and moves together with the movable portion.

Resistance value detection unit 120 detects a resistance value of resistor 118, detects the position of the movable portion based on the result of detection, and detects the degree of bending of linear body 1 based on the result of detection.

According to such a configuration, adaptation to a measurement device in which high resolution or high frequency response is required can be achieved. In addition, unlike the optical sensor, compressive force P can accurately be measured even though linear body 1 is transparent. Moreover, unlike the optical sensor, compressive force P can accurately be measured even though the measurement device is used in an adverse environment such as in the water and in the oil.

Embodiment 12

Figure 26:
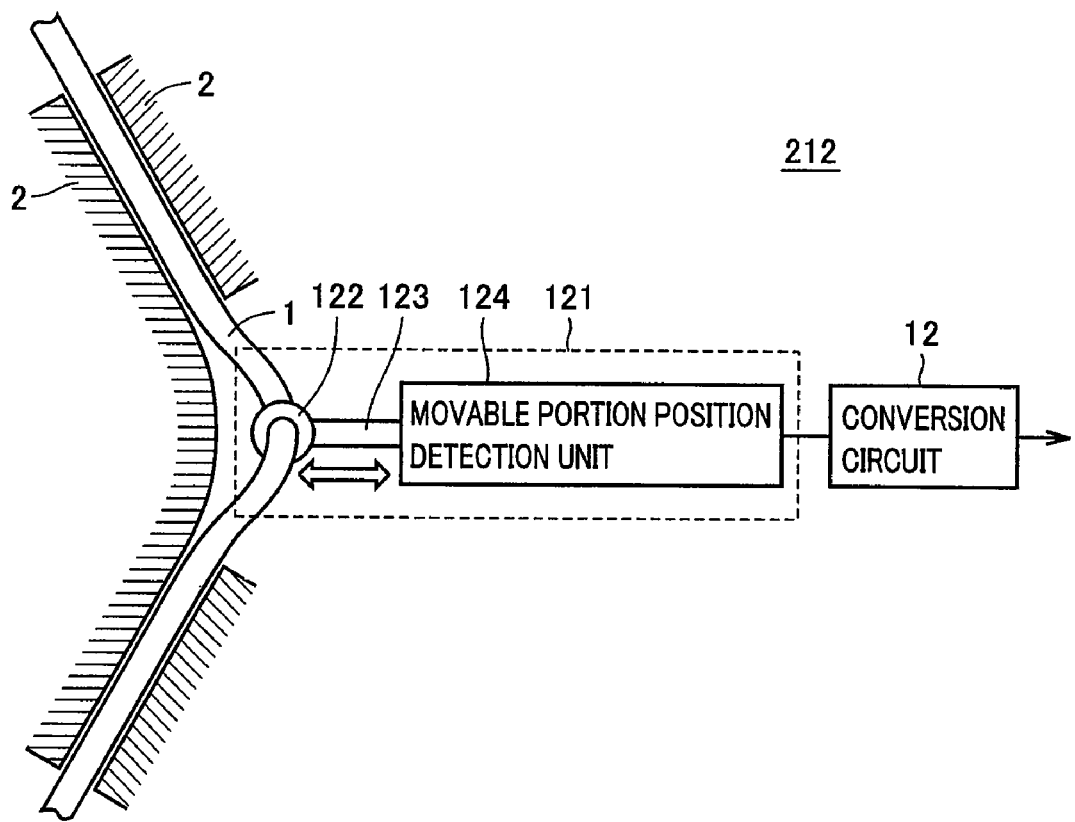
FIG. 26 is a schematic diagram showing a configuration of a measurement device according to Embodiment 12 representing one embodiment of the present invention.

FIG. 26 is a schematic diagram showing a configuration of a measurement device according to Embodiment 12 representing one embodiment of the present invention.

Referring to FIG. 26, a measurement device 212 includes measurement device main body 2, a contact sensor 121, and conversion circuit 12. Contact sensor 121 includes a ring 122, a connection portion 123, and a movable portion position detection unit 124. Ring 122 and connection portion 123 form the movable portion.

Linear body 1 passes through ring 122. Ring 122, that is, the movable portion, moves together with bending of linear body 1.

Movable portion position detection unit 124 detects a position of the movable portion and detects the degree of bending of linear body 1 based on the result of detection.

Conversion circuit 12 converts the degree of bending of linear body 1 detected by movable portion position detection unit 124 to an electric signal indicating compressive force P for output.

Movable portion position detection unit 124 may be any of an optical type, a magnetic type, a resistance type, and a differential transformer type, and movable portion position detection unit 124 adapted to these types is configured similarly to that in Embodiment 11, and therefore, detailed description will not be repeated here.

According to such a configuration, adaptation to a measurement device in which high frequency response is required can be achieved. In addition, unlike the optical sensor, compressive force P can accurately be measured even though linear body 1 is transparent. Moreover, unlike the optical sensor, compressive force P can accurately be measured even though the measurement device is used in an adverse environment such as in the water and in the oil.

Embodiment 13

Figure 27:
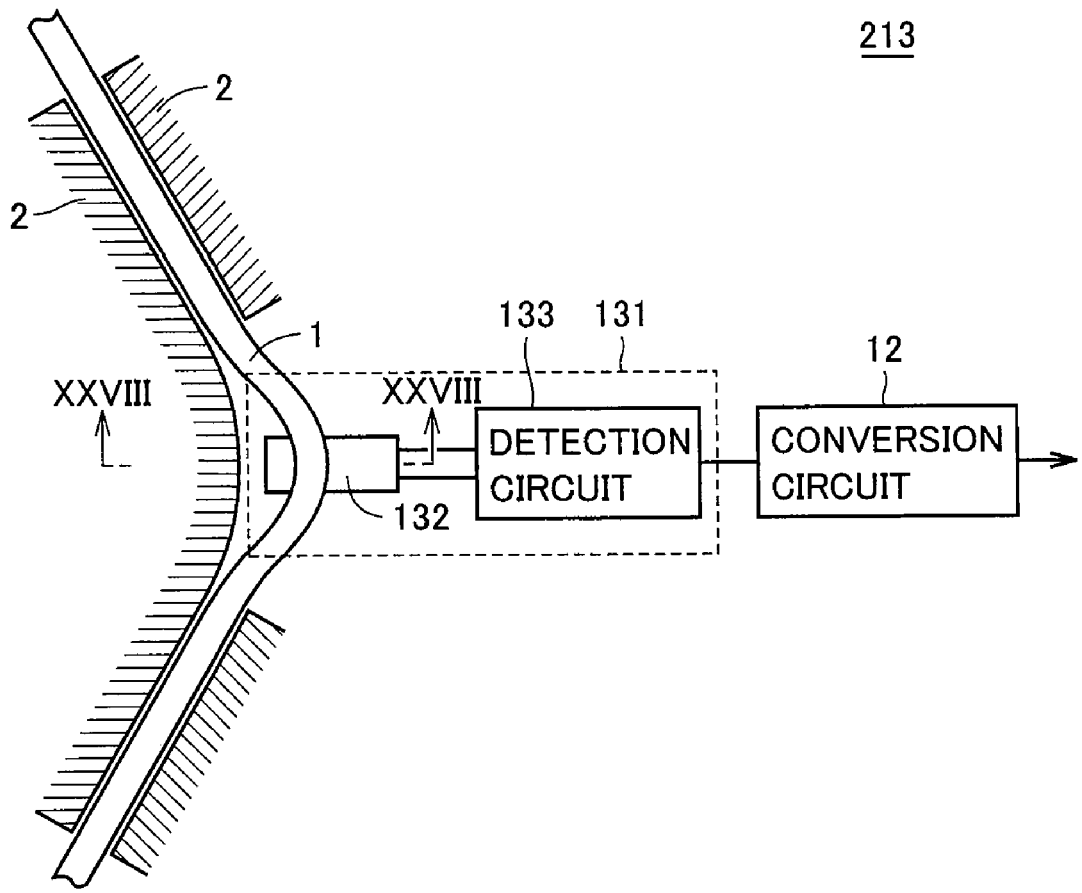
FIG. 27 is a schematic diagram showing a configuration of a measurement device according to Embodiment 13 representing one embodiment of the present invention.
Figure 28:
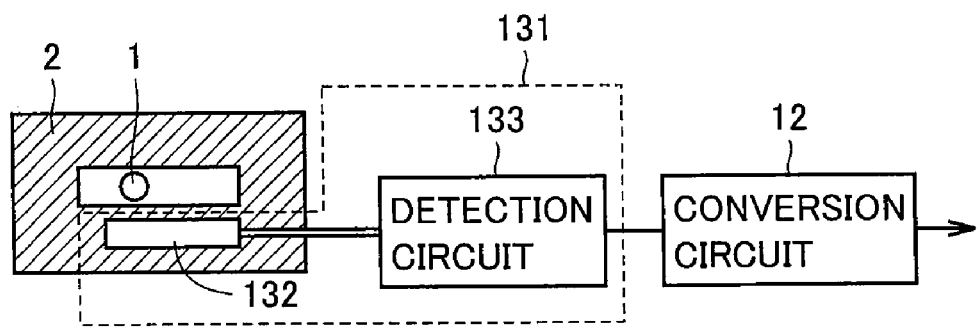
FIG. 28 is a cross-sectional view showing a cross-section along the line XXVIII-XXVIII in FIG. 27.

FIG. 27 is a schematic diagram showing a configuration of a measurement device according to Embodiment 13 representing one embodiment of the present invention. FIG. 28 is a cross-sectional view showing a cross-section along the line XXVIII-XXVIII in FIG. 27.

Referring to FIGS. 27 and 28, a measurement device 213 includes measurement device main body 2, a displacement sensor 131, and conversion circuit 12. Displacement sensor 131 includes a measurement unit 132 and a detection circuit 133. Displacement sensor 131 corresponds to capacitance sensor 42 shown in FIG. 16, eddy current sensor 81 shown in FIG. 20, or magnetic sensor 91 shown in FIG. 21. More specifically, measurement unit 132 corresponds to detection electrode 43, detection coil 82, or detection coil 92. Detection circuit 133 corresponds to capacitance detection circuit 45, waveform detection circuit 84, or waveform detection circuit 94.

In the measurement devices according to Embodiments 1 to 12, the displacement sensor is arranged in the direction of bending of linear body 1. In the present embodiment, however, displacement sensor 131 is arranged in a direction substantially perpendicular to the direction of bending of linear body 1.

According to such a configuration as well, displacement sensor 131 can detect the degree of bending of linear body 1.

Embodiment 14

Figure 29:
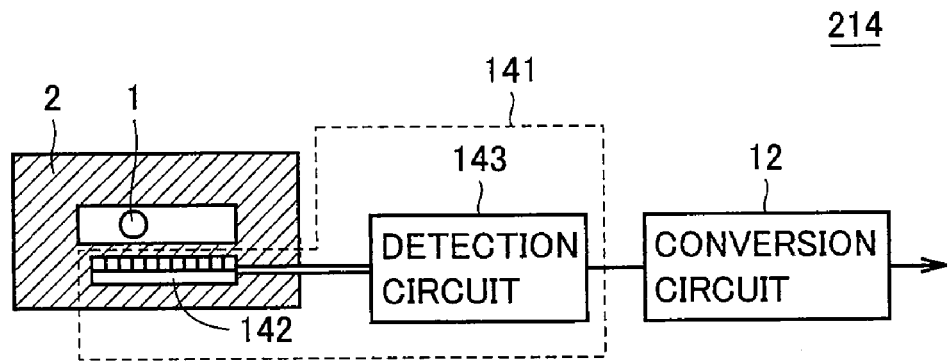
FIG. 29 is a cross-sectional view showing a configuration of a measurement device according to Embodiment 14 representing one embodiment of the present invention.

FIG. 29 is a cross-sectional view showing a configuration of a measurement device according to Embodiment 14 representing one embodiment of the present invention.

Referring to FIG. 29, a measurement device 214 includes measurement device main body 2, a displacement sensor 141, and conversion circuit 12. Displacement sensor 141 includes a measurement unit 142 and a detection circuit 143.

Measurement unit 142 is implemented by arranging a plurality of measurement units 132 shown in FIG. 28 in an array.

Detection circuit 143 performs a prescribed operation on the result of measurement by the plurality of measurement units 142 and detects the degree of bending of linear body 1.

As the configuration and the operation are otherwise the same as those of the measurement device according to Embodiment 13, detailed description will not be repeated here.

According to such a configuration, compressive force P can more accurately be measured.

Embodiment 15

Figure 30:
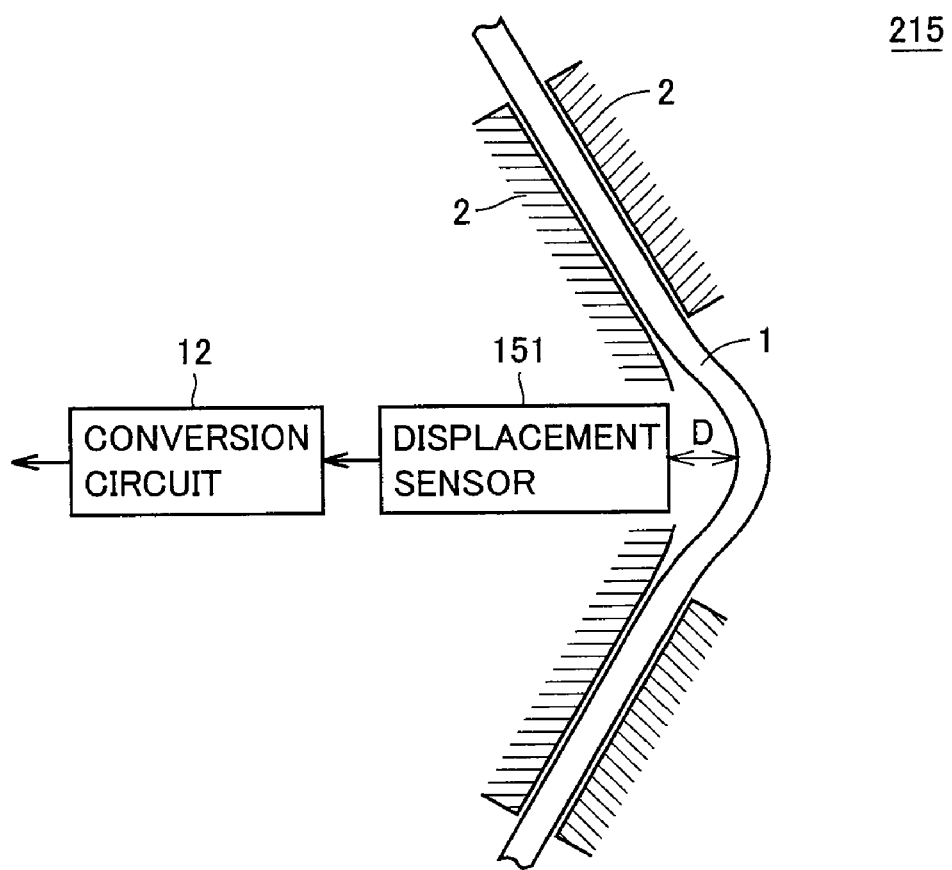
FIG. 30 is a schematic diagram showing a configuration of a measurement device according to Embodiment 15 representing one embodiment of the present invention.

FIG. 30 is a schematic diagram showing a configuration of a measurement device according to Embodiment 15 representing one embodiment of the present invention.

Referring to FIG. 30, a measurement device 215 includes measurement device main body 2, a displacement sensor 151, and conversion circuit 12.

In the present embodiment, displacement sensor 151 is arranged in a direction opposite to the direction of bending of linear body 1. Displacement sensor 151 detects a distance D between displacement sensor 151 and the bending portion of linear body 1. Detection of distance D is equivalent to measurement of height h of the bending portion.

Conversion circuit 12 stores the result of determination in advance of correlation between compressive force P in the direction of longitudinal axis applied to linear body 1 and distance D, that is, the degree of bending of linear body 1. Conversion circuit 12 converts detected distance L into compressive force P by using the stored correlation.

Embodiment 16

Figure 31:
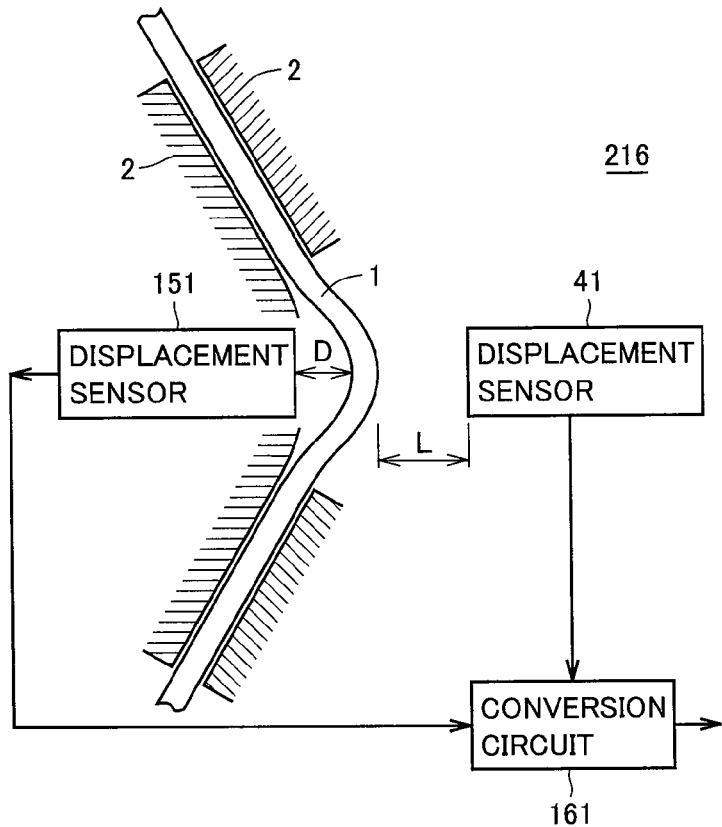
FIG. 31 is a schematic diagram showing a configuration of a measurement device according to Embodiment 16 representing one embodiment of the present invention.

FIG. 31 is a schematic diagram showing a configuration of a measurement device according to Embodiment 16 representing one embodiment of the present invention.

Referring to FIG. 31, a measurement device 216 includes measurement device main body 2, displacement sensor 41, displacement sensor 151, and a conversion circuit 161.

Displacement sensor 41 is arranged in the direction of bending of linear body 1. Displacement sensor 41 detects distance L between displacement sensor 41 and the bending portion.

Displacement sensor 151 is arranged in the direction opposite to the direction of bending of linear body 1. Displacement sensor 151 detects distance D between displacement sensor 151 and the bending portion.

Conversion circuit 161 stores the result of determination in advance of correlation of compressive force P in the direction of longitudinal axis applied to linear body 1 with distance L and distance D. Conversion circuit 161 converts detected distances L and D into compressive force P by using the stored correlation.

According to such a configuration, compressive force P can more accurately be measured.

Embodiment 17

Figure 32:
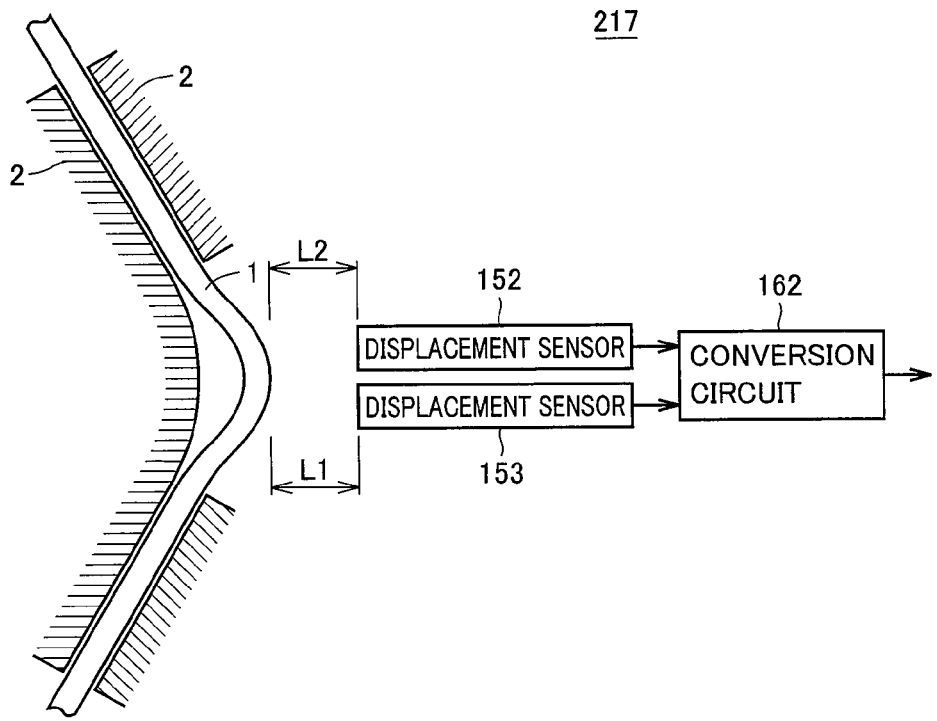
FIG. 32 is a schematic diagram showing a configuration of a measurement device according to Embodiment 17 representing one embodiment of the present invention.

FIG. 32 is a schematic diagram showing a configuration of a measurement device according to Embodiment 17 representing one embodiment of the present invention.

Referring to FIG. 32, a measurement device 217 includes measurement device main body 2, displacement sensors 152 and 153, and a conversion circuit 162.

Displacement sensors 152 and 153 are arranged in the direction of bending of linear body 1. Displacement sensors 152 and 153 detect distances L1 and L2 from the bending portion respectively.

Conversion circuit 162 stores the result of determination in advance of correlation of compressive force P in the direction of longitudinal axis applied to linear body 1 with distance L1 and distance L2. Conversion circuit 162 converts detected distances L1 and L2 into compressive force P by using the stored correlation.

According to such a configuration, compressive force P can more accurately be measured.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

INDUSTRIAL APPLICABILITY

The measurement device and the measurement method according to the present invention are particularly advantageously applicable as a device and a method for measuring compressive force applied to a linear body having flexibility, such as a linear medical appliance to be inserted in a vessel in a body.

The invention claimed is:

1. A measurement device for measuring an amount of compressive force applied in a direction of a longitudinal axis of a linear body having flexibility, comprising:
    a main body including a through hole through which said linear body passes is formed, and within said main body a portion of said linear body undergoes bending which displaces said portion of said linear body with respect to said main body in a prescribed direction in response to said compressive force being applied to said linear body;
    a sensor which detects a degree of said bending of said portion of said linear body; and
    a conversion circuit which determines said amount of compressive force based on the detected degree of bending.

2. The measurement device according to claim 1, wherein said linear body is a linear medical appliance to be inserted in a vessel in a body.

3. The measurement device according to claim 1, wherein said sensor is an optical sensor including a light source emitting light and a light receiver receiving light emitted by said light source, and detecting said degree of bending of said linear body using a quantity of light received by said light receiver-with respect to a quantity of light emitted by said light source.

4. The measurement device according to claim 1, wherein said sensor is an optical array sensor including a light source emitting light and a light receiver receiving light emitted by said light source, and detecting said degree of bending of said linear body by detecting a position at which light emitted by said light source is cut off by said linear body and a quantity of light received by said light receiver decreases.

5. The measurement device according to claim 1, wherein said sensor includes a detection electrode and a capacitance detection circuit-detecting the degree of bending of said linear body based on a capacitance generated between said detection electrode and said linear body.

6. The measurement device according to claim 1, wherein said sensor includes
    a light source,
    an objective lens directing light from said light source to said linear body,
    a moving portion moving said objective lens,
    an objective lens position detection unit detecting a position of said objective lens,
    a light receiver receiving light reflected by said linear body and converting the light into an electric signal, and an operation unit detecting the degree of bending of said linear body based on detected said position of said objective lens and said electric signal from said light receiver.

7. The measurement device according to claim 1, wherein said sensor includes a light source emitting light to said linear body, and an image processing unit receiving light reflected by said linear body, picking up an image of said linear body, and detecting the degree of bending of said linear body based on picked-up said image of said linear body.

8. The measurement device according to claim 1, wherein said sensor includes a piezoelectric element outputting ultrasound to said linear body and receiving the ultrasound reflected by said linear body, and a time difference detection unit detecting a time period from output of the ultrasound by said piezoelectric element to said linear body until reception of the ultrasound reflected by said linear body and detecting the degree of bending of said linear body based on detected said time period.

9. The measurement device according to claim 1, wherein said linear body is a conductor or a magnetic element, and said sensor further includes a coil, a voltage supply circuit supplying a voltage to said coil, and a waveform detection circuit detecting an amplitude of a waveform of a current that flows through said coil or a phase difference between a waveform of the voltage supplied to said coil and the waveform of the current that flows through said coil, and detecting the degree of bending of said linear body based on a result of detection.

10. The measurement device according to claim 1, wherein said linear body is a magnetic element, and said sensor further includes a magnet and a magnetic detection unit detecting magnetic flux from said magnet and detecting the degree of bending of said linear body based on a result of detection.

11. The measurement device according to claim 1, wherein said sensor further includes a movable portion coupled to said linear body, and a movable portion position detection unit detecting a position of said movable portion and detecting the degree of bending of said linear body based on a result of detection.

12. The measurement device according to claim 1, comprising a plurality of said sensors; wherein said conversion circuit converts said degree of bending detected by said plurality of sensors into said compressive force applied to said linear body.

13. The measurement device according to claim 1, comprising at least any one of a visualizing instrument displaying an output from said sensor and an auralizing instrument converting variation in said output into voice and sound.

14. The measurement device according to claim 1, incorporated in medical equipment for use.

15. The measurement device according to claim 1, attached to a training simulator simulating a human body for use.

16. A method of measuring an amount of compressive force applied in a direction of a longitudinal axis of a linear body having flexibility, comprising the steps of:

detecting, by using a sensor, a degree of bending of said linear body in a prescribed direction when said compressive force is applied to said linear body; and determining said amount of compressive force based on the degree of bending detected in said detecting step and a predetermined correlation between bending of said linear body and compressive force applied to said linear body.

17. The measurement device according to claim 1, where the linear body has a diameter around 0.35 mm.

* * * * *

UNITED STATES PATENT AND TRADEMARK OFFICE
CERTIFICATE OF CORRECTION

PATENT NO. : 7,984,659 B2
APPLICATION NO. : 12/293323
DATED : July 26, 2011
INVENTOR(S) : Hideo Fujimoto et al.

It is certified that error appears in the above-identified patent and that said Letters Patent is hereby corrected as shown below:

Title Page, Item (73) Assignees: it currently reads, National University Corporation Nagoya, Aichi (JP); Institute of Technology NTN Corporation, Osaka (JP) but it should read -- National University Corporation Nagoya Institute of Technology Aichi, Japan; NTN Corporation Osaka, Japan.

Signed and Sealed this
Thirteenth Day of March, 2012

David J. Kappos
*Director of the United States Patent and Trademark Office*